(12) United States Patent
Biechele et al.

(10) Patent No.: US 11,819,553 B2
(45) Date of Patent: Nov. 21, 2023

(54) GLYPICAN 3 ANTIBODIES AND CONJUGATES THEREOF

(71) Applicant: Seagen Inc., Bothell, WA (US)

(72) Inventors: Travis Biechele, Seattle, WA (US); William Arthur, Bainbridge Island, WA (US); Patrick Burke, Seattle, WA (US); Lori Westendorf, Snohomish, WA (US)

(73) Assignee: Seagen Inc., Bothell, WA (US)

( * ) Notice: Subject to any disclaimer, the term of this patent is extended or adjusted under 35 U.S.C. 154(b) by 405 days.

(21) Appl. No.: 16/970,095

(22) PCT Filed: Feb. 15, 2019

(86) PCT No.: PCT/US2019/018182
§ 371 (c)(1),
(2) Date: Aug. 14, 2020

(87) PCT Pub. No.: WO2019/161174
PCT Pub. Date: Aug. 22, 2019

(65) Prior Publication Data
US 2021/0361776 A1 Nov. 25, 2021

Related U.S. Application Data

(60) Provisional application No. 62/631,353, filed on Feb. 15, 2018.

(51) Int. Cl.
*A61P 35/00* (2006.01)
*A61K 31/454* (2006.01)
*A61K 47/68* (2017.01)
*C07K 16/30* (2006.01)
*A61K 39/00* (2006.01)

(52) U.S. Cl.
CPC ........ *A61K 47/6859* (2017.08); *A61K 31/454* (2013.01); *A61K 47/6803* (2017.08); *A61P 35/00* (2018.01); *C07K 16/303* (2013.01); *A61K 2039/505* (2013.01); *C07K 2317/24* (2013.01); *C07K 2317/92* (2013.01)

(58) Field of Classification Search
CPC .............. A61K 47/6859; A61K 31/454; A61K 47/6803; A61K 2039/505; A61P 35/00; C07K 16/303; C07K 2317/24; C07K 2317/92; C07K 2317/565
USPC ...................................................... 424/174.1
See application file for complete search history.

(56) References Cited

U.S. PATENT DOCUMENTS

| 7,427,400 B2 | 9/2008 | Bergstein |
| 7,744,880 B2 | 6/2010 | Aburatani et al. |
| 2006/0167232 A1 | 7/2006 | Aburatani et al. |

(Continued)

FOREIGN PATENT DOCUMENTS

| EP | 2216046 A2 | 8/2010 |
| WO | WO2015/179658 A2 | 11/2015 |

(Continued)

OTHER PUBLICATIONS

Toader, "Antibody-Drug Conjugates", Topics in Medicinal Chemistry, vol. 28, pp. 289-332, (2017).

(Continued)

*Primary Examiner* — Yan Xiao
(74) *Attorney, Agent, or Firm* — Seagen Inc.

(57) ABSTRACT

The invention provides murine, chimeric, and humanized antibodies that specifically bind to GPC3 and conjugates thereof.

21 Claims, 13 Drawing Sheets

Specification includes a Sequence Listing.

(56) References Cited

U.S. PATENT DOCUMENTS

2010/0248359 A1    9/2010   Nakano et al.
2012/0321617 A1   12/2012   Osterroth et al.
2017/0073426 A1    3/2017   Ohtomo et al.
2017/0326249 A1   11/2017   Pan et al.
2018/0312602 A1   11/2018   Polakis et al.

FOREIGN PATENT DOCUMENTS

| WO | WO2015/179658 A3 | 11/2015 |
| WO | WO2016001275 A1 | 1/2016 |
| WO | WO2016/040684 A1 | 3/2016 |
| WO | WO2017181109 A1 | 10/2017 |
| WO | WO2017/196764 A1 | 11/2017 |
| WO | WO2019/161174 A1 | 8/2019 |

OTHER PUBLICATIONS

EP Application No. 19755133.6, Extended Search Report, 9 pages, dated Oct. 29, 2021.
PCT Application No. PCT/US2019/018182, International Search Report and Written Opinion dated Jul. 5, 2019, 15 pages.
PCT Application No. PCT/US2019/018182, International Report on Patentability dated Aug. 27, 2020, 8 pages.

FIGURE 1

GLYPICAN 3 ANTIBODIES AND CONJUGATES THEREOF

CROSS REFERENCE TO RELATED APPLICATIONS

This application is a U.S. national stage filing under 35 USC § 371 of International Application No. PCT/US2019/018182, filed Feb. 15, 2019, which claims the benefit of priority to U.S. Application No. 62/631,353, filed Feb. 15, 2018 each of which are incorporated by reference in their entirety.

REFERENCE TO A SEQUENCE LISTING

This application includes an electronic sequence listing in a file named 4700-111US_Sequence Listing_ST25.txt, created on Apr. 24, 2024 and containing 38 KB, which is hereby incorporated by reference.

BACKGROUND

Glypican 3 (GPC3) is a cell surface proteoglycan that is known to be expressed on hepatocellular carcinoma cells and has been reported on a number of malignant cells. The present invention provides GPC3 antibodies and conjugates thereof.

SUMMARY OF THE CLAIMED INVENTION

Provided herein are anti-GPC3 antibodies and GPC3 directed antibody-drug conjugates. In particular, provided herein are GPC3 directed tubulysin antibody-drug conjugates and methods of using such conjugates to treat GPC3 expressing disorders. Preferred anti-GPC3 antibodies are chimeric or humanized forms of the murine GPC3-1 antibody. The murine GPC3-1 antibody comprises a heavy chain variable region having the amino acid sequence set forth in SEQ ID NO:8 and a light chain variable region having the amino acid sequence set forth in SEQ ID NO:9.

BRIEF DESCRIPTION OF THE FIGURES

Figure 1:
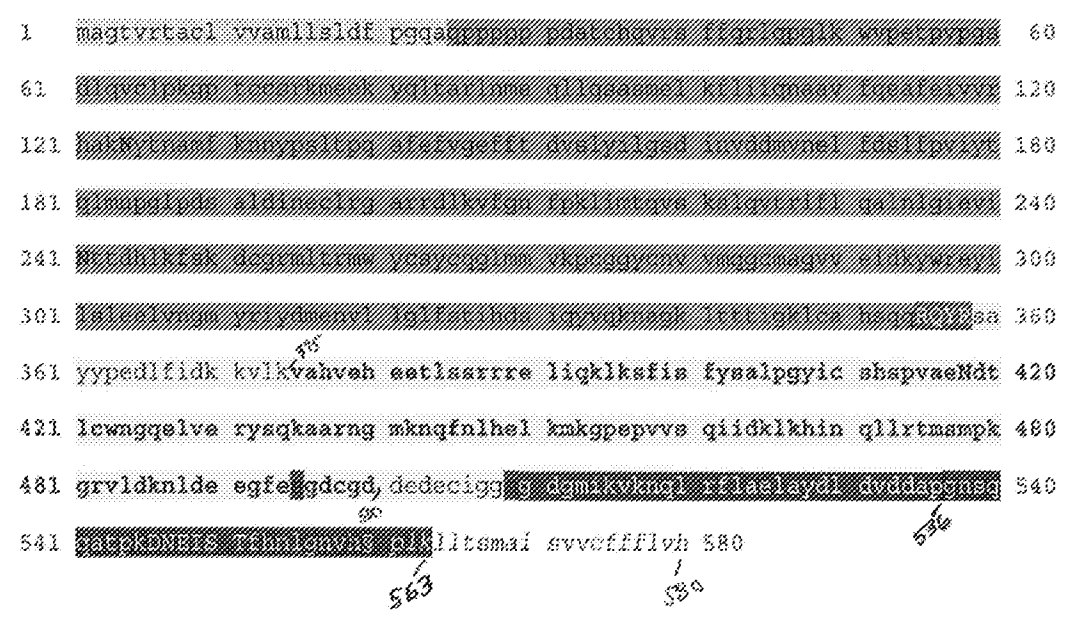

FIG. 1 shows the sequence of human GPC3 (SEQ ID NO. 30).

DEFINITIONS

Figure 2:
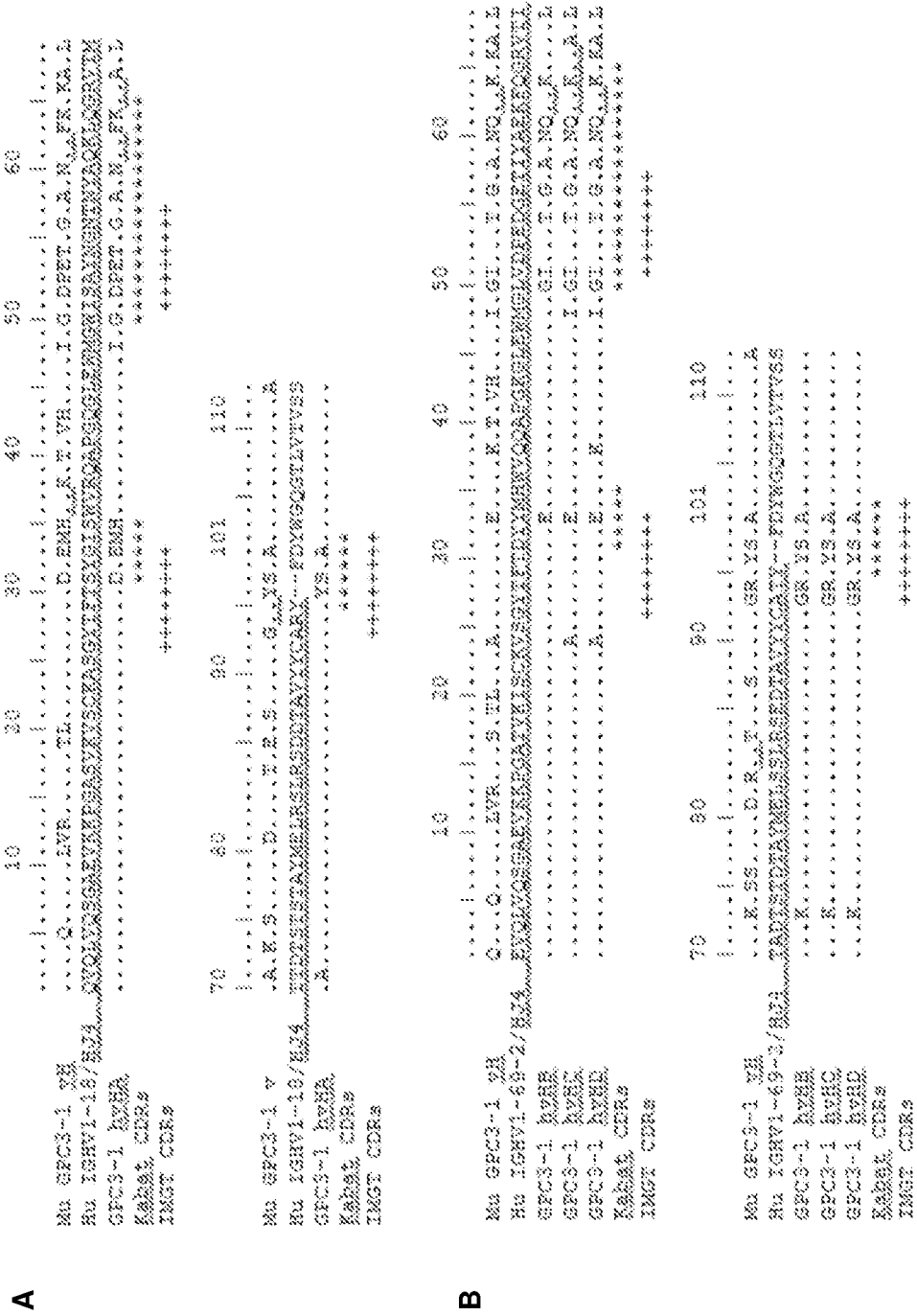
FIG. 2A shows a sequence alignment of hGPC3-1 heavy chain variants with human vH donor sequence, HV1-18/HJ4.
FIG. 2B shows a sequence alignment of hGPC3-1 heavy chain variants with human vH donor sequence, HV1-69-2/HJ4.
Figure 3:
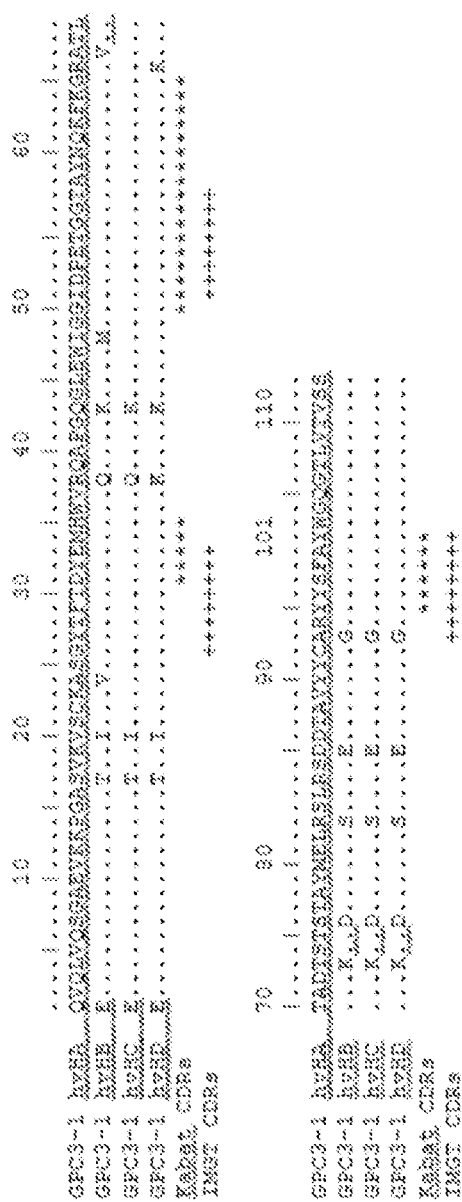
FIG. 3 shows a sequence alignment of hGPC3-1 heavy chain variants.
Figure 4:
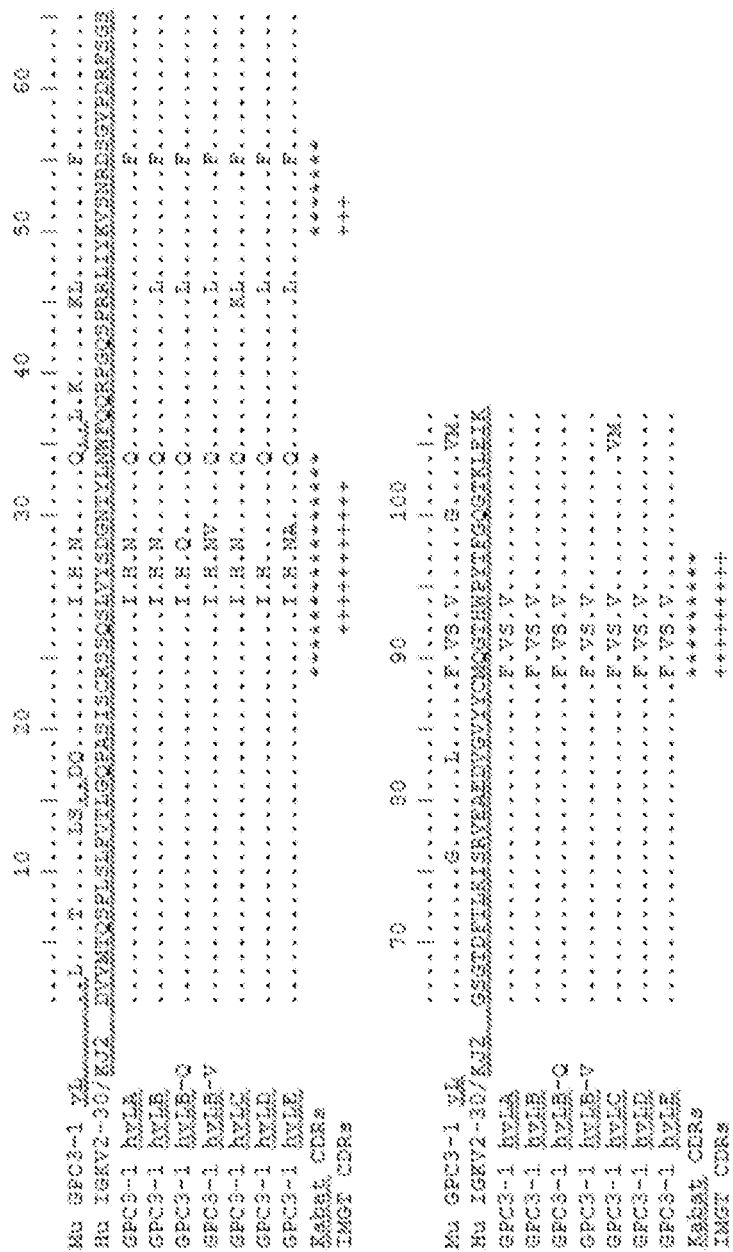
FIG. 4 shows a sequence alignment of hGPC3-1 light chain variants with human vL donor sequence, KV2-30/KJ2.
Figure 5:
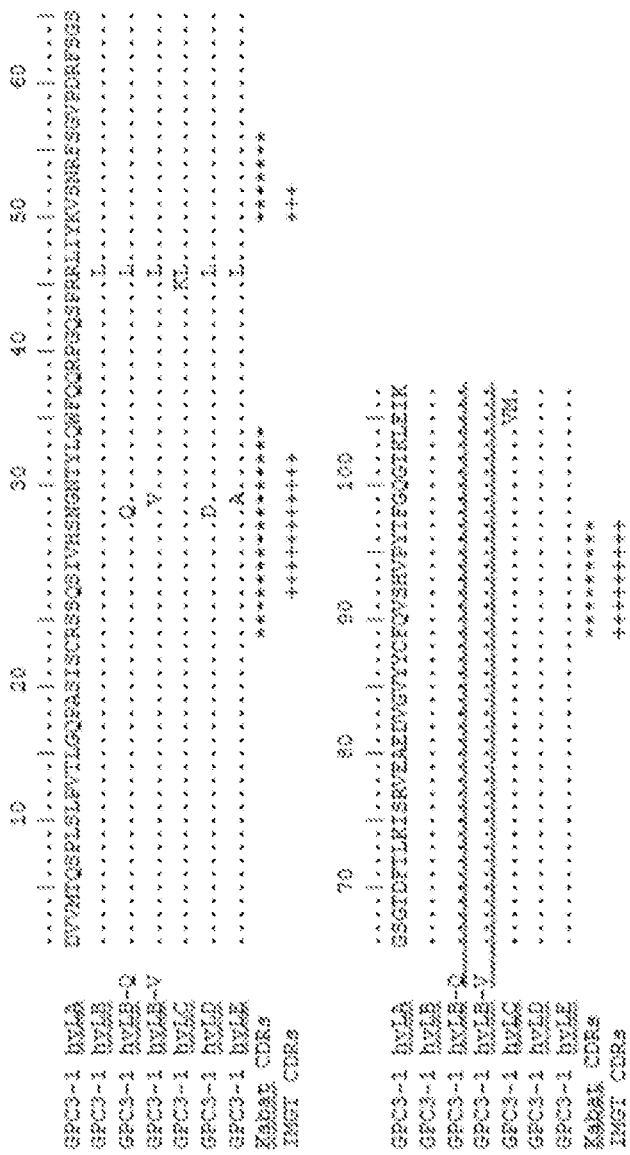
FIG. 5 shows a sequence alignment of hGPC3-1 light chain variants.

The term "monoclonal antibody" as used herein refers to an antibody obtained from a population of substantially homogeneous antibodies, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, for example, U.S. Pat. No. 4,816,567). The "monoclonal antibodies" may also be isolated from phage antibody libraries using the techniques described in Clackson et al. (1991) *Nature*, 352:624-628 and Marks et al. (1991) *J. Mol. Biol.*, 222:581-597, for example or may be made by other methods. The antibodies described herein are monoclonal antibodies.

Antibodies are typically provided in isolated form. This means that an antibody is typically at least 50% w/w pure of interfering proteins and other contaminants arising from its production or purification but does not exclude the possibility that the antibody is combined with an excess of pharmaceutical acceptable carrier(s) or other vehicle intended to facilitate its use. Sometimes antibodies are at least 60%, 70%, 80%, 90%, 95 or 99% w/w pure of interfering proteins and contaminants from production or purification. Antibodies, including isolated antibodies, can be conjugated to cytotoxic agents and provided as antibody drug conjugates.

An "isolated" polynucleotide refers to a polynucleotide that has been identified and separated and/or recovered from components of its natural.

Specific binding of a monoclonal antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. The GPC3 directed antibody-drug conjugates and anti-GPC3 antibodies specifically bind to GPC3.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region, means a light chain variable region without the light chain signal peptide. Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the subscript and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989, Ch. 7, incorporated by reference in its entirety for all purposes). The mature variable regions of each light/heavy chain pair form the antibody binding site. Thus, an intact antibody has two binding sites. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, MD, 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering system) in which corresponding residues between different heavy chain variable regions or between different light chain variable regions are assigned the same number. Numbering of the heavy chain constant region is via the EU index as set forth in Kabat (Kabat, *Sequences of Proteins of Immunological Interest* (National Institutes of Health, Bethesda, MD, 1987 and 1991).

The term "antibody" includes intact antibodies and antigen binding fragments thereof. An "intact antibody" is one which comprises an antigen-binding variable region as well as a light chain constant domain ($C_L$) and heavy chain constant domains, $C_H1$, $C_H2$, $C_H3$ and $C_H4$, as appropriate for the antibody class. The constant domains may be native sequence constant domains (e.g., human native sequence constant domains) or amino acid sequence variant thereof. Antibody fragments compete with the intact antibody from which they were derived for specific binding to the target including separate heavy chains, light chains Fab, Fab', F(ab')$_2$, F(ab)c, diabodies, Dabs, nanobodies, and Fv. Fragments can be produced by recombinant DNA techniques, or by enzymatic or chemical separation of intact immunoglobulins. The term "antibody" also includes a diabody (homodimeric Fv fragment) or a minibody ($V_L$-$V_H$-$C_H3$), a bispecific antibody or the like. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

The term "therapeutically effective amount" or 'effective amount" refers to an amount of the antibody-drug conjugate that is effective to treat a disease or disorder in a mammal. In the case of cancer, a therapeutically effective amount of the conjugate may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit tumor growth; and/or relieve one or more of the symptoms associated with the cancer. For cancer therapy, efficacy can, for example, be measured by assessing the time to disease progression (TTP) and/or determining the response rate (RR). The term "effective regimen" refers to a combination of amount of the conjugate being administered and dosage frequency adequate to accomplish treatment of the disorder.

The terms "treat" or "treatment," unless otherwise indicated by context, refer to therapeutic treatment wherein the object is to inhibit or slow down (lessen) an undesired physiological change or disorder, such as the development or spread of cancer. Beneficial or desired clinical results include, but are not limited to, alleviation of symptoms, diminishment of extent of disease, a stabilized (i.e., not worsening) state of disease, delay or slowing of disease progression, amelioration or palliation of the disease state, and remission (whether partial or complete), whether detectable or undetectable. "Treatment" can also mean prolonging survival as compared to expected survival if not receiving treatment. Those in need of treatment include those with detectable disease. Those in need of treatment can also include those with undetectable disease, e.g., patients that have achieved a complete response after treatment for the GPC3 expressing disorder but are in need of therapy in order to prevent relapse.

"Compound" as the term is used herein, unless otherwise stated or implied by context, refers to and encompasses the chemical compound itself, either named or represented by structure, and salt form(s) thereof, whether explicitly stated or not, unless context makes clear that such salt forms are to be excluded. Compound salts include zwitterionic salt forms and acid addition and base addition salt forms having organic counterions or inorganic counterions and salt forms involving two or more counterions, which may be the same or different. In some aspects, the salt form is a pharmaceutically acceptable salt form of the compound. The term "compound" further encompasses solvate forms of the compound, in which solvent is noncovalently associated with the compound or is reversibly associated covalently with the compound, as when a carbonyl group of the compound is hydrated to form a gem-diol. Solvate forms include those of the compound itself and its salt form(s) and are inclusive of hemisolvates, monosolvates, disolvates, including hydrates; and when a compound can be associated with two or more solvent molecules, the two or more solvent molecules may be the same or different. In some instances, a compound of the invention will include an explicit reference to one or more of the above forms, e.g., salts and solvates, which does not imply any solid state form of the compound; however, this reference is for emphasis only, and is not to be construed as excluding any other of the forms as identified above. Furthermore, when explicit reference to a salt and/or solvate form of a compound or an Antibody Drug Conjugate composition is not made, that omission is not to be construed as excluding the salt and/or solvate form(s) of the compound or Conjugate unless context make clear that such salt and/or solvate forms are to be excluded.

"Moiety", as the term is used herein, unless otherwise stated or implied by context, means a specified segment, fragment, or functional group of a molecule or compound. Chemical moieties are sometimes indicated as chemical entities that are embedded in or appended to (i.e., a substituent or variable group) a molecule, compound or chemical formula.

Unless indicated otherwise or implied by context, for any substituent group or moiety described herein by a given range of carbon atoms, the designated range means that any individual number of carbon atoms is described. Thus, reference to, e.g., "optionally substituted $C_1$-$C_4$ alkyl" or "optionally substituted $C_2$-$C_6$ alkenyl" specifically means that a 1, 2, 3, or 4 carbon alkyl moiety, optionally substituted, as defined herein, is present, or a 2, 3, 4, 5, or 6 carbon alkenyl moiety, optionally substituted, as defined herein, is present, respectively. All such numerical designations are expressly intended to disclose all of the individual carbon atom groups; and thus "optionally substituted $C_1$-$C_4$ alkyl" includes, methyl, ethyl, 3-carbon alkyls, and 4-carbon alkyls, including all of their positional isomers, whether substituted or unsubstituted. Thus, when an alkyl moiety is substituted, the numerical designations refer to an unsubstituted base moiety and are not intended to include carbon atoms not directly attached to the base moiety that may be present in the substituents of that base moiety. For esters, carbonates, carbamates, and ureas as defined herein that are identified by a given range of carbon atoms, the designated range includes the carbonyl carbon of the respective functional group. Thus, a $C_1$ ester refers to a formate ester and a $C_2$ ester refers to an acetate ester.

The organic substituents, moieties, and groups described herein, and for other any other moieties described herein, usually will exclude unstable moieties except where such unstable moieties are transient species that one can use to make a compound with sufficient chemical stability for the one or more of the uses described herein. Substituents, moieties or groups by operation of the definitions provided herein that results in those having a pentavalent carbon are specifically excluded.

"Alkyl" as the term is used herein, by itself or as part of another term, unless otherwise stated or implied by context, refers to methyl or a collection of contiguous carbon atoms, one of which is monovalent, wherein one or more of the carbon atoms are saturated (i.e., is comprised of one or more $sp^3$ carbons) and are covalently linked together in normal, secondary, tertiary or cyclic arrangements, i.e., in a linear, branched, cyclic arrangement or some combination thereof. When the contiguous saturated carbon atoms are in a cyclic arrangement such alkyl moieties are, in some aspects, referred to as carbocyclyls.

When referring to an alkyl moiety as an alkyl substituent, that alkyl substituent to a Markush structure or another organic moiety with which it is associated is methyl or that chain of contiguous carbon atoms covalently attached to the structure or moiety through a $sp^3$ carbon of the alkyl substituent. An alkyl substituent, as used herein, therefore contains at least one saturated moiety and may additionally contain one or more independently selected double bonds and/or triple bonds to define an unsaturated alkyl moiety, and may also be substituted by 1 to 4, typically 1 to 3, or 1 or 2 other moieties that include appropriate optional substituent(s) as described herein. The number of carbon atoms in a saturated alkyl moiety can vary and typically is 1-8, 1-6 or 1-4 and in an unsaturated alkyl moiety typically varies between 3-8, 3-6 or 3-4.

Unless otherwise indicated or implied by context, the term "alkyl" will indicate a saturated, non-cyclic hydrocarbon radical, wherein the hydrocarbon radical has the indicated number of covalently linked saturated carbon atoms so that terms such as "$C_1$-$C_6$ alkyl" or "$C_1$-$C_6$ alkyl" means an alkyl moiety or group containing 1 saturated carbon atom (i.e., is methyl) or 2, 3, 4, 5 or 6 contiguous, non-cyclic saturated carbon atoms and "$C_1$-$C_8$ alkyl" refers to an alkyl moiety or group having 1 saturated carbon atom or 2, 3, 4, 5, 6, 7 or 8 contiguous saturated, non-cyclic carbon atoms.

When a saturated alkyl substituent, moiety or group is specified, species include those derived from removing a hydrogen atom from a parent alkane (i.e., an alkyl moiety is monovalent) and may include methyl, ethyl, 1-propyl (n-propyl), 2-propyl (iso-propyl, —CH(CH$_3$)$_2$), 1-butyl (n-butyl), 2-methyl-1-propyl (iso-butyl, —CH$_2$CH(CH$_3$)$_2$), 2-butyl (sec-butyl, —CH(CH$_3$)CH$_2$CH$_3$), 2-methyl-2-propyl (t-butyl, —C(CH$_3$)$_3$), amyl, isoamyl, sec-amyl and other linear and branch chain alkyl moieties.

"Alkylene," as the term is used herein, by itself of as part of another term, unless otherwise stated or implied by context, refers to a saturated, branched or straight chain hydrocarbon diradical, substituted or unsubstituted, wherein one or more of the carbon atoms is saturated (i.e., is comprised of one or more $sp^3$ carbons), of the stated number of carbon atoms typically ranging from 1 to 8, 1 or 6, or 1 to 4 carbon atoms and having two radical centers (i.e., is divalent). Those radical centers are derivable by removal of two hydrogen atoms from the same or two different saturated (i.e., $sp^3$) carbon atoms of a parent alkane or from an alkyl radical as described herein in which a hydrogen atom has been removed from another of its saturated carbons or from the radical carbon of an alkyl radical to form a diradical.

An alkylene moiety is exemplified without limitation by methylene (—CH$_2$—), 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), and like diradicals. Typically, an alkylene is a branched or straight chain hydrocarbon containing only sp³ carbons (i.e., is fully saturated notwithstanding the radical carbon atoms) and in some aspects is unsubstituted. In other aspects, an alkylene contains an internal site of unsaturation(s) in the form of one or more double and/or triple bond functional groups, typically 1 or 2, more typically 1, such functional groups so that the terminal carbons of the unsaturated alkylene moiety are monovalent sp³ carbon atoms. In still other aspects, the alkylene is unsubstituted or is substituted with 1 to 4, typically 1 to 3, or 1 or 2 substituents, as defined herein for optional substituents.

"Optionally substituted alkyl" or "optionally substituted phenyl" as used herein, unless otherwise stated or implied by context, refer to an alkyl or phenyl substituent, moiety or group as defined herein wherein hydrogen atom(s) of that substituent, moiety or group has been optionally replaced with different moiety(ies) or group(s) and include those selected from the group consisting of cyano, halogen, —$CX_3$, wherein X is independently halogen, an N-linked moiety and an O-linked moiety as defined herein.

Typically, optional substituents that are present are selected from the group consisting of —X, —Cl, —OH, —OR'—OC(=O)R', —$NH_2$, —NH(R'), —NR'(R')$_2$, —N(R')$_3$, —$CF_3$, —CN, and —$NO_2$, wherein each X is independently a halogen, and each R' is independently $C_1$-$C_6$ alkyl.

"O-linked moiety" as used herein refers to an oxygen-containing organic moiety that is directly attached to a Markush structure or another moiety to which it is associated through its oxygen atom. An O-linked moiety includes —OH, acyloxy (i.e., —OC(=O)$R^a$, in which $R^a$ is typically —H, optionally substituted alkyl or optionally substituted phenyl, and ether groups such as a $C_1$-$C_6$ alkyloxy, wherein the alkyl moiety is saturated or unsaturated. Other exemplary O-linked substituents are provided by the definition for carbamate.

"N-linked moiety" as used herein refers to an nitrogen-containing organic moiety that is directly attached to a Markush structure or another moiety to which it is associated through its nitrogen atom. An N-linked moiety includes —$NH_2$, —$NHR^a$, —$N(R^a)_2$ and amide (i.e., —$NR^aC$(=O)$R^a$) in which $R^a$ is typically selected from the group consisting of —H, optionally substituted $C_1$-$C_6$ alkyl and optionally substituted phenyl. Other exemplary N-linked substituents are provided by definitions for carbamate.

"Carbamate" as used here means a substituent, moiety or group that contains a carbamate functional group represented by —O—C(=O)N($R^a$)— or —O—C(=O)N($R^a$)$_2$, wherein $R^a$, independently selected, is hydrogen, or an optionally substituted $C_1$-$C_6$ alkyl and include —O—C(=O)NH (optionally substituted alkyl) or —O—C(=O)N (optionally substituted alkyl)$_2$, which are exemplary carbamate substituents, wherein the optionally substituted alkyl are independently selected optionally substituted $C_1$-$C_6$ alkyl, and. When carbamate is used as a Markush group (i.e., a substituent), the singly bonded oxygen (O-linked) or nitrogen (N-linked) of the carbamate functional group is attached to a Markush formula with which it is associated. The linkage of the carbamate substituent is either explicitly stated (N- or O-linked) or implicit in the context to which this substituent is referred. O-linked carbamates described herein are exemplary monovalent O-linked moieties and N-linked carbamates are exemplary N-linked moieties.

"Halogen" or "halo" as used herein means fluorine, chlorine, bromine or iodine and is typically —F or —Cl.

"Salt thereof" as the phrase is used herein, unless otherwise stated or implied by context, refers to a salt form of a compound (e.g., a Drug, a Drug Linker compound or an Antibody Drug Conjugate compound). A salt form of a compound is of one or more internal salt forms and/or involves the inclusion of another molecule such as an acetate ion, a succinate ion or other counterion. The counterion in a salt form of a compound is typically an organic or inorganic moiety that stabilizes the charge on the parent compound. A salt form of a compound has one or more than one charged atoms in its structure. In instances where multiple charged atoms are part of the salt form, multiple counter ions and/or multiple charged counter ions are present. Hence, a salt form of a compound typically has one or more charged atoms corresponding to those of the non-salt form of the compound and one or more counterions. In some aspects, the non-salt form of a compound contains at least one amino group or other basic moiety, and accordingly in the presence of an acid, an acid addition salt of the basic moiety is obtained. In other aspects, the non-salt form of a compound contains at least one carboxylic acid group or other acidic moiety, and accordingly in the presence of a base, a carboxylate or other anionic moiety is obtained.

Exemplary counteranion and countercations in compound salt forms include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2-hydroxy-3-naphthoate)) salts.

Selection of a salt form of a compound is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability under accelerated conditions (i.e., for determining degradation or solid-state changes when stored at 40° C. and 75% relative humidity).

The term "pharmaceutically acceptable" means approved or approvable by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an antibody or antibody-drug conjugate is administered to a subject.

A "pharmaceutically acceptable salt" is a salt form of a compound that is suitable for administration to a subject as described herein and in some aspects includes countercations or counteranions as described by P. H. Stahl and C. G. Wermuth, editors, *Handbook of Pharmaceutical Salts: Properties, Selection and Use*, Weinheim/Zurich:Wiley-VCH/VHCA, 2002.

Solvates in the context of the invention are those forms of the compounds of the invention that form a complex through coordination with solvent molecules. Hydrates are one specific form of solvates, in which the coordination takes place with water. Preferred solvates in the context of the present invention are hydrates.

"Tubulysin compound" as used herein (unless otherwise stated or implied by context) is a tetrapeptide-based tubulin disrupting agent having cytotoxic or cytostatic activity, and is characterized by an un-natural amino acid residue having a central 5-membered nitrogen-containing heteroarylene moiety and an N-terminal pipecolic acid residue, which in some aspects contains a tertiary amine which may be used for incorporation into an Antibody Drug Conjugate as a quaternized Drug Unit. Non-limiting exemplary tubulysins suitable for quaternization have the structure of:

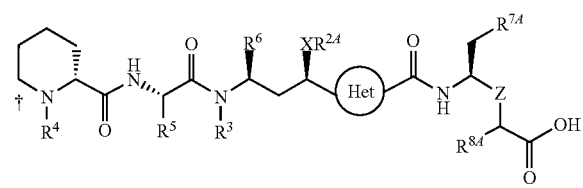

or a salt thereof, in particular a pharmaceutically acceptable salt, wherein the indicated nitrogen atom is the site of quaternization when the tubulysin compound is incorporated into a quaternized Drug Unit; the circle represents the 5-membered nitrogen-containing heteroarylene moiety, wherein the shown substituents to that heteroaryl are in a 1,3-relationship to each other with optional substitution at the remaining positions; X is O, S, or $NR^{2B}$; $R^3$, $R^4$, $R^5$ and $R^6$ are independently optionally substituted $C_1$-$C_6$ alkyl, $R^{7A}$ is optionally substituted phenyl; $R^{2B}$ and $R^{8A}$ are independently hydrogen or optionally substituted $C_1$-$C_6$ alkyl; Z is —$CH_2$—, —$CH_2CH_2$— or —CH=CH—, and $R^{2A}$ is hydrogen or optionally substituted $C_1$-$C_6$ alkyl, or —$XR^{2A}$ represents a monovalent O-linked substituent or a monovalent N-linked substituent.

Exemplary methods of preparing tubulysin drugs and structure-activity relationships are provided by Shankar et al. "Synthesis and structure-activity relationship studies of novel tubulysin U analogs-effect on cytotoxicity of structural variations in the tubuvaline fragment" *Org. Biomol. Chem.* (2013) 11: 2273-2287; Xiangming et al. "Recent advances in the synthesis of tubulysins" *Mini-Rev. Med. Chem.* (2013) 13: 1572-8; Shankar et al. "Synthesis and cytotoxic evaluation of diastereomers and N-terminal analogs of Tubulysin-U" *Tet. Lett.* (2013) 54: 6137-6141; Shankar et al. "Total synthesis and cytotoxicity evaluation of an oxazole analogue of Tubulysin U" *Synlett* (2011) 2011(12): 1673-6; Raghavan et al. *J. Med. Chem.* (2008) 51: 1530-3; Balasubramanian, R. et al. "Tubulysin analogs incorporating desmethyl and dimethyl tubuphenylalanine derivatives" *Bioorg. Med. Chem. Lett.* (2008) 18: 2996-9; and Raghavan et al. "Cytotoxic simplified tubulysin analogues" *J. Med. Chem.* (2008) 51: 1530-3.

In some aspects tubulysins suitable for quaternization include those having the structure of:

or a salt thereof, in particular a pharmaceutically acceptable salt, wherein $R^{2A}$ is methyl, ethyl or propyl or —C(=O)$R^{2B}$, wherein $R^{2B}$ is a previously defined; and $R^{7B}$ is hydrogen or —OH. In other aspects the tubulysins suitable for quaternization is tubulysin M, which has the above structure in which $R^{2A}$ is —C(=O)$CH_3$ and $R^{7B}$ is hydrogen or is a tubulysin compound having the above structure in which $R^{2A}$ is ethyl and $R^{7B}$ is hydrogen.

"Quaternized tubulysin drug unit" as used herein (unless otherwise stated or implied by context) relates to a tertiary amine-containing tubulysin compound in which its tertiary amine nitrogen is present in the quaternized Drug Unit structure as a quaternary amine salt and the quaternized Drug Unit upon its release from a drug linker moiety of an Antibody Drug Conjugate provides the free tertiary amine-containing tubulysin compound. In some aspects, a quaternized tubulysin Drug Unit ($D^+$) is obtained by condensing the tertiary amine nitrogen of the C-terminal component of a tubulysin compound with Linker Unit precursor having a suitable leaving group. In other aspects the C-terminal component is first quaternized with the remainder of the tubulysin compound then appended to complete the $D^+$ Unit. Therefore, structures containing a quaternized tubulysin Drug Unit imply no particular method in which $D^+$ was formed and does not require that a reactant used in its formation be a tertiary-amine containing drug, but only require $D^+$ to be incorporate or correspond to the structure of the tertiary-amine containing intended to be released from a Antibody Drug Conjugate compound.

"Stretcher Unit" as used herein, unless otherwise stated or implied by context, refers to a component of a Linker Unit in a glucuronide-based drug linker moiety of an Antibody Drug Conjugate that intervenes between the Linker Unit's succinic acid moiety or hydrolyzed form thereof, which is attached to the antibody, and the Glucuronide Unit. Alternatively, a Stretcher Unit refers to a component of a Linker Unit in a glucuronide-based Drug Linker Compound, which can be used in the preparation of an Antibody Drug Conjugate, that intervenes between the maleimide moiety of the Linker Unit and the Glucuronide Unit. A Stretcher Unit (A) can be a single unit or can contain multiple subunits. Typically, A one distinct unit or has 2 to 4 distinct subunits.

In some aspects, the Stretcher Unit or first subunit thereof is comprised of an optionally substituted $C_1$-$C_6$ alkylene having one of its divalent centers attached to the nitrogen atom of the maleimide or succinimide moiety or hydrolyzed form thereof, and the other attached to a carbonyl residue, wherein sometimes an optional substituent of the $C_1$-$C_6$ alkylene is present as a Basic Unit to provide for a self-stabilizing linker as described in WO 2013/173337. When A has 2 or more distinct subunits, the second subunit is typically a -$L^P$(PEG) moiety, wherein $L^P$ is a Parallel

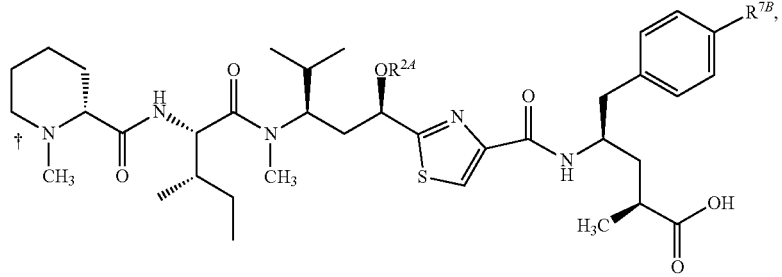

Connector Unit comprised of a tri-functional amine-containing amino acid residue and PEG is a PEG Unit as defined herein, or an α-amino acid, β-amino acid or other amine-containing acid residue. In either instance the amine nitrogen atom of the amine-containing acid residue of the second subunit is attached to the carbonyl residue of the first subunit and the carbon atom of the carbonyl residue of the second subunit is bonded to a Glucuronide Unit of a glucuronide-based Linker Unit or to the amine nitrogen atom of a third subunit of A, which typically is another amine-containing acid residue in which its carbonyl residue is bonded to a Glucuronide Unit of a glucuronide-based Linker Unit.

"Parallel Connector Unit" as the term is used herein, unless otherwise stated or implied by context, is a trifunctional organic moiety in a Linker Unit of a drug linker moiety of an Antibody Drug Conjugate or in a Linker Unit of a Drug Linker compound having a hydrophobic Drug Unit in which one of the trifunctional groups is attached to a PEG Unit and the other two are attach the Parallel Connector ($L^P$) Unit within the Linker Unit, such that the PEG Unit is capable of a "parallel" orientation to a hydrophobic Drug Unit so as to mask, at least in part, its hydrophobicity. The PEG Unit attached to $L^P$ contains a repeating number of ethylene glycol subunits, typically ranging from 8 to 24, to provide for that masking. $L^P$, PEG and hydrophobic Drug Units are further described by WO 2015/057699, the disclosure of which are incorporated by reference herein.

"Glucuronide Unit" as the term is used herein, unless otherwise stated or implied by context, is a cleavable component of a Linker Unit attached to the Drug Unit of a glucuronide-based drug linker moiety of an Antibody Drug Conjugate or a Drug Linker compound and is comprised of an amino benzyl residue and a carbohydrate residue bonded thereto through a glycosidic bond, wherein the benzyl residue is capable of self-immolation upon enzymatic action by a glycosidase at that glycosidic bond for release of the Drug Unit as free drug. In some aspects, a quaternized Drug Unit, such as a quaternized tubulysin Drug Unit as defined herein, is covalently attached to the benzylic carbon atom of the aminobenzyl moiety having the nitrogen atom of its amino residue covalently attached to the remainder of the Linker Unit and having its arylene residue substituted with the glycosidic-bonded carbohydrate residue, such as a glucuronic acid residue, wherein the carbohydrate residue is in an ortho or para relationship with the benzyl carbon atom, so that upon cleavage of the glycosidic bond by a glycosidase the benzyl moiety undergoes spontaneous fragmentation to release the quaternized Drug Unit as a free tertiary-containing drug. In other aspects, a carbamate functional group intervenes between the benzylic carbon atom and an amine nitrogen atom of an non-quaternized amine-containing Drug Unit in which the monovalent oxygen atom of the carbamate functional group is covalently attached to the benzylic carbon atom. In those aspects, a Drug Unit is released containing a carbamic acid functional group, which undergoes spontaneous loss of $CO_2$ to provide the free amine-containing drug. Glucuronide Units attached to non-quaternized Drug Units are further described by WO 2007/011968, and Glucuronide Units attached to quaternized Drug Units are further described by WO2016/040684.

Unless otherwise apparent from the context, the term "about" encompasses values within a standard deviation of a stated value.

DETAILED DESCRIPTION

I. General

The present invention is based, in part, on the discovery that antibody-drug conjugates, including antibody-drug conjugates targeted to human GPC3 are particularly effective at killing GPC3+ expressing cells. In particular, it was found that a high affinity GPC3-1 humanized antibody could be constructed using as the heavy chain variable region acceptor sequence, the germline hIGHv1-18 or hIGHV1-26-2 and J exon $J_H$-4, and for the light chain variable region acceptor sequence, the germline hIGKv2-30 and J exon $J_K$-2, and by mutating residues at one or more key sites back to the murine antibody or murine germline sequence. For the heavy chain, these key sites included one or more of positions H24, H38, H48, H66, H67, H69, H71, H73, H93, and H94. For the light chain, these key sites included one or more of positions L45, L46, L105, and L106. The GPC3-1 humanized antibody was effective at drug delivery as part of an antibody drug conjugate (ADC). When conjugated to a SGD-6859 tubulysin M drug-linker, the resultant hGPC3-1ec tubulysin M conjugate (hGPC3-1ec SGD-6859) was highly active against a panel of HCC cell lines. The "ec" designation following hGPC3-1 indicates that the antibody has a cysteine substitution at position 239 of the heavy chain (numbering is by the EU index as set forth in Kabat).

The hGPC3-1ec SGD-6859 ADC can target GPC3-expressing tumors such as hepatocellular carcinoma (HCC). HCC has been classified as generally resistant to chemotherapy. This is due to high expression of drug efflux transporters in HCC cells. These transformers efficiently exclude systemic chemotherapeutics. Tubulysin M is a poor substrate for drug efflux transporters and is thus an effective drug-linker for HCC-targeting ADCs. Furthermore, tubulysin M is sufficiently cell permeable to have adequate bystander activity.

II. Antibodies of the Invention

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence.

Thus, a humanized antibody is an antibody having some or all CDRs entirely or substantially from a non-human donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and diabodies, a humanized antibody typically comprises a humanized heavy chain and a humanized light chain. A CDR in a humanized or human antibody is substantially from or substantially identical to a corresponding CDR in a non-human antibody when at least 60%, 85%, 90%, 95% or 100% of corresponding residues (as defined by Kabat) are identical between the respective CDRs. In some embodiments, a CDR in a humanized antibody or human antibody is substantially from or substantially identical to a corresponding CDR in a non-human antibody when there are no more than 3 conservative amino acid substitutions in each CDR. The variable region framework sequences of an antibody chain or the constant region of an antibody chain are substantially from a human variable region framework sequence or human constant region respectively when at least 70%, 80%, 85%, 90%, 95% or 100% of corresponding residues defined by Kabat are identical. In some humanized antibodies of the present invention, there are at least three and up to nine murine GPC3-1 backmutations in the heavy chain variable framework region of the antibody and up to four murine GPC3-1 backmutations in the light chain variable region of the antibody.

Although humanized antibodies often incorporate all six CDRs (preferably as defined by Kabat) from a mouse antibody, they can also be made with less than all CDRs (e.g., at least 3, 4, or 5) CDRs from a mouse antibody (e.g., Pascalis et al., *J. Immunol.* 169:3076, 2002; Vajdos et al., *Journal of Molecular Biology*, 320: 415-428, 2002; Iwahashi et al., *Mol. Immunol.* 36:1079-1091, 1999; Tamura et al, *Journal of Immunology*, 164:1432-1441, 2000).

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

The invention provides antibodies directed against the human GPC3 antigen. Preferred antibodies are chimeric or humanized antibodies derived from the murine GPC3-1 antibody. A preferred acceptor sequence for the heavy chain variable region is the germline hIGHV1-18 or hIGHV1-69-2 and J exon JH4. For the light chain variable region, a preferred acceptor sequence is the germline hIGKV2-30 and J exon JK2.

An exemplary anti-GPC3 antibody is a humanized antibody that includes the heavy chain CDRs as set forth in SEQ ID NO:1 and the light chain CDRs as set forth in SEQ ID NO:2 and additionally has a mature heavy chain variable region with at least 80%, 85%, 90%, 91%, 92%, 93%, 94% or 95% identity to SEQ ID NO:1 and a mature light chain variable region with at least 80%, 85%, 90%, 91%, 92%, 93%, 94% or 95% identity to SEQ ID NO:2. The CDRs are as defined by Kabat. Preferably, the following amino acid residues of the heavy chain variable domain framework are maintained: H24 is occupied by V, H38 is occupied by Q, H48 is occupied by M, H66 is occupied by R, H67 is occupied by V, H69 is occupied by L, H71 is occupied by A, H73 is occupied by K, H93 is occupied by G, H94 is occupied by R, and the following amino acid residues of the light chain are maintained: L45 is occupied by R, L46 is occupied by L, L105 is occupied by E, L106 is occupied by I.

Accordingly, provided herein are humanized antibodies that comprise a heavy chain variable region as set forth in SEQ ID NO:1 and a light chain variable region as set forth in SEQ ID NO:2 provided that H24 is occupied by V or A, H38 is occupied by Q, R or K, H48 is occupied by M or I, H66 is occupied by R or K, H67 is occupied by V or A, H69 is occupied by L, H71 is occupied by A, H73 is occupied by K or T, H93 is occupied by G or A, H94 is occupied by R and the following amino acid residues of the light chain are present: L45 is occupied by R or K, L46 is occupied by L or R, L105 is occupied by E or V, L106 is occupied by I or M.

Humanized forms of the mouse GPC3-1 antibody include four exemplified humanized heavy chain mature variable regions (HA-HD) and seven exemplified humanized light chain mature variable regions (LA-LE, LB-Q, LB-V). The permutations of these chains include HALA, HALB, HALC, HBLA, HBLB, HBLC, HBLD, HBLE, HBLB-Q, HBLB-V, HCLA, HCLB, HCLC, HDLA, HDLB and HDLC. Of these permutations, HBLE is preferred. HBLE comprises the heavy chain set forth in SEQ ID NO:1 and light chain set forth in SEQ ID NO:2. Any one of HALA, HALB, HALC, HBLA, HBLB, HBLC, HBLD, HBLE, HBLB-Q, HBLB-V, HCLA, HCLB, HCLC, HDLA, HDLB and HDLC can be used, however, in place of HBLE.

In some aspects, the apparent dissociation constant (kd) of the humanized GPC3-1 antibodies for human GPC3 is preferably within a range of 0.1 nM to 10 nM, even more preferably within a range of 0.1 nM to 5 nM, even preferably within a range of 1 nM to 3 nM or 2 nM to about 3 nM. In some aspect, the antibodies of the present invention have an apparent dissociation constant within a range of 0.1 to 1.5 times, or even 0.5 to 2 times that of the apparent dissociation constant of the murine GPC3-1 antibody for human GPC3. In some aspects, the apparent dissociation constant (kd) of the antibodies for humanized GPC3-1 is about 2.7.

A. Selection of Constant Region

Heavy and light chain variable regions of humanized GPC3-1 antibodies can be linked to at least a portion of a human constant region. The choice of constant region can depend, in part, whether antibody-dependent cell-mediated cytotoxicity, antibody dependent cellular phagocytosis and/or complement dependent cytotoxicity are desired. For example, human isotopes IgG1 and IgG3 have strong complement-dependent cytotoxicity, human isotype IgG2 has weak complement-dependent cytotoxicity and human IgG4 lacks complement-dependent cytotoxicity. Human IgG1 and IgG3 also induce stronger cell mediated effector functions than human IgG2 and IgG4. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain subscript domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

The constant region can be modified to allow for site specific conjugation of a drug-linker. Such techniques include the use of naturally occurring or engineered cysteine residues, disulfide bridges, poly-histidine sequences, glycoengineering tags, and transglutaminase recognition sequences. An exemplary substitution for site specific conjugation using bacterial transglutaminase is N297S or N297Q. An exemplary substitution for site specific conjugation using an engineered cysteine is S239C (US 20100158909; numbering of the Fc region is according to the EU index). In some aspects, the presence of an additional cysteine residue allows interchain disulfide bond formation. Such interchain disulfide bond formation can cause steric hindrance, thereby reducing the affinity of the Fc region-FcγR binding interaction. The cysteine residue(s) introduced in or in proximity to the Fc region of an IgG constant region can also serve as sites for conjugation to therapeutic agents (i.e., coupling cytotoxic drugs using thiol specific reagents such as maleimide derivatives of drugs. The presence of a therapeutic agent causes steric hindrance, thereby further reducing the affinity of the Fc region-FcγR binding interaction. Antibody fragments can also be modified for site-specific conjugation of a drug-linker, see for example, Kim et al., *Mol Cancer Ther* 2008; 7(8).

B. Expression of Recombinant Antibodies

Humanized or chimeric GPC3-1 antibodies can be produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

Mammalian cells are a preferred host for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed in the art, and include CHO cell lines (e.g., DG44), various COS cell lines, HeLa cells, HEK293 cells, L cells, and non-antibody-producing myelomas including Sp2/0 and NS0. Preferably, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Once expressed, antibodies can be purified according to standard procedures of the art, including HPLC purification, column chromatography, gel electrophoresis and the like (see generally, Scopes, Protein Purification (Springer-Verlag, NY, 1982)).

III. Nucleic Acids

The invention further provides nucleic acids encoding any of the humanized heavy and light chains described herein. Typically, the nucleic acids also encode a signal peptide fused to the mature heavy and light chain variable regions. Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

In one embodiment, this disclosure provides an isolated polynucleotide encoding an antibody heavy chain variable region comprising the amino acid sequence as set forth in HA, HB, HC, or HD. For example, the isolated polynucleotide can encode an antibody heavy chain variable region comprising the amino acid sequence of SEQ ID NO:1. This isolated polynucleotide can further encode a human IgG heavy chain constant region. The isotype of the IgG constant region is, e.g., IgG1, IgG2, IgG3, or IgG4. In one embodiment, the isotype of the IgG constant region is IgG1. In another embodiment, the encoded IgG1 constant region has an amino acid sequence comprising a substitution at residue 239, according to the EU index as set forth in Kabat system, i.e., S239C. The disclosure also provides an expression vector comprising the isolated polynucleotide encoding the antibody heavy chain variable region comprising the amino acid sequence as set forth in HA, HB, HC, or HD (e.g., SEQ ID NO:1 or variants thereof), and further, a host cell comprising that expression vector. In some embodiments, the host cell is a mammalian host cell, e.g., a CHO cell.

In another embodiment, this disclosure provides an isolated polynucleotide encoding an antibody light chain variable region comprising the amino acid sequence as set forth in LA, LB, LC, LD, LE, LB-Q, or LB-V. For example, an isolated polynucleotide encoding an antibody light chain variable region comprising the amino acid sequence of SEQ ID NO:2. This isolated polynucleotide can further encode a human IgG light chain constant region. The isotype of the IgG light chain constant region is, e.g., a kappa constant region. The disclosure also provides an expression vector comprising the isolated polynucleotide encoding the antibody light chain variable region comprising the amino acid sequence as set forth in LA, LB, LC, LD, LE, LB-Q, or LB-V (e.g., SEQ ID NO:2 or variants thereof), and further, a host cell comprising that expression vector. In some embodiments, the host cell is a mammalian host cell, e.g., a CHO cell.

In another embodiment, this disclosure provides an isolated polynucleotide or polynucleotides encoding an antibody heavy chain variable region comprising the amino acid sequence of SEQ ID NO:1 and an antibody light chain variable region comprising the amino acid sequence of SEQ ID NO:2, the heavy chain variable domain and the light chain variable domain forming an antibody or antigen binding fragment that specifically binds to human GPC3. This disclosure also provides an expression vector comprising the isolated polynucleotide or polynucleotides the encode the antibody heavy chain variable region comprising the amino acid sequence of SEQ ID NO:1 and the antibody light chain variable region comprising the amino acid sequence of SEQ ID NO:2. A host cell comprising the expression vector or vectors is also provided. The host cell is preferably a mammalian cell, e.g., a CHO cell.

In another embodiment, this disclosure provides first and second vectors comprising a polynucleotide encoding an antibody heavy chain variable region comprising the amino acid sequence of SEQ ID NO:1 and a polynucleotide encoding an antibody light chain variable region comprising the amino acid sequence of SEQ ID NO:2, the heavy chain variable domain and the light chain variable domain forming an antibody or antigen binding fragment that specifically binds to human GPC3. Host cell comprising the vectors are provided, preferably mammalian host cells, such as a CHO cell.

IV. Antibody-Drug Conjugates

Anti-GPC3 antibodies can be conjugated to cytotoxic moieties or cytostatic moieties to form antibody-drug conjugates (ADCs). Particularly suitable moieties for conjugation to antibodies are cytotoxic agents (e.g., chemotherapeutic agents), prodrug converting enzymes, radioactive isotopes or compounds, or toxins (these moieties being collectively referred to as a therapeutic agent). For example, an anti-GPC3 antibody can be conjugated to a cytotoxic agent such as a chemotherapeutic agent, or a toxin (e.g., a cytostatic or cytocidal agent such as, for example, abrin, ricin A, *pseudomonas* exotoxin, or diphtheria toxin). Examples of useful classes of cytotoxic agents include, for example, DNA minor groove binders, DNA alkylating agents, and microtubule disrupting agents. Exemplary cytotoxic agents include, for example, tubulysins, auristatins, camptothecins, calicheamicins, duocarmycins, etoposides, maytansinoids (e.g., DM1, DM2, DM3, DM4), taxanes, benzodiazepines (e.g., pyrrolo[1,4]benzodiazepines, indolinobenzodiazepines, and oxazolidinobenzodiazepines) and vinca alkaloids. Exemplary antibody-drug conjugates include tubulysin based antibody-drug conjugates meaning that the drug component is an tubulysin drug, auristatin based antibody-drug conjugates meaning that the drug component is an auristatin drug, maytansinoid antibody-drug conjugates meaning that the drug component is a maytansinoid drug, and benzodiazepine antibody drug conjugates meaning that the drug component is a benzodiazepine (e.g., pyrrolo[1,4]benzodiazepines, indolinobenzodiazepines, and oxazolidinobenzodiazepines).

Techniques for conjugating therapeutic agents to antibodies, are well-known. (See, e.g., Alley et al., Current Opinion in Chemical Biology 2010 14:1-9; Senter, Cancer J., 2008, 14(3):154-169.) The therapeutic agent can be conjugated in a manner that reduces its activity unless it is cleaved off the antibody (e.g., by hydrolysis, by proteolytic degradation, or by a cleaving agent). In some aspects, the therapeutic agent is attached to the antibody with a cleavable linker that is sensitive to cleavage in the intracellular environment of the GPC3-expressing cancer cell but is not substantially sensitive to the extracellular environment, such that the conjugate is cleaved from the antibody when it is internalized by the GPC3-expressing cancer cell (e.g., in the endosomal or, for example by virtue of pH sensitivity or protease sensitivity, in the lysosomal environment or in the caveolear environment). In some aspects, the therapeutic agent can also be attached to the antibody with a non-cleavable linker.

The present inventors have unexpectedly found that a GPC3 targeted ADC comprising a quaternized tubulysin drug-linker is effective for treating GPC3-expressing disorders, particularly when the linker unit is comprised of a glucuronide unit.

A glucuronide-based linker is a hydrophilic alternative to protease cleavable linkers, such as valine-citrulline and valine-alanine and exploits intracellular beta glucuronidase to initiate drug release. Also cysteine variants (and dual cysteine variants) at position 239 or 239/295 or 294 are particularly suitable for conjugation to hydrophobic drugs such as tubulysin M because the site of conjugation proximate to glycan residues serves to mask the hydrophobic drug. Tubulysins and glucuronide linkers attached to tubulysins are more fully described in WO2016040684. In an embodiment, the GPC targeted ADC releases unmodified tubulysin M into the cell after internalization.

Accordingly, a preferred glucuronide-based drug linker compound having a quaternized tubulysin drug unit for use in the present invention has the structure of:

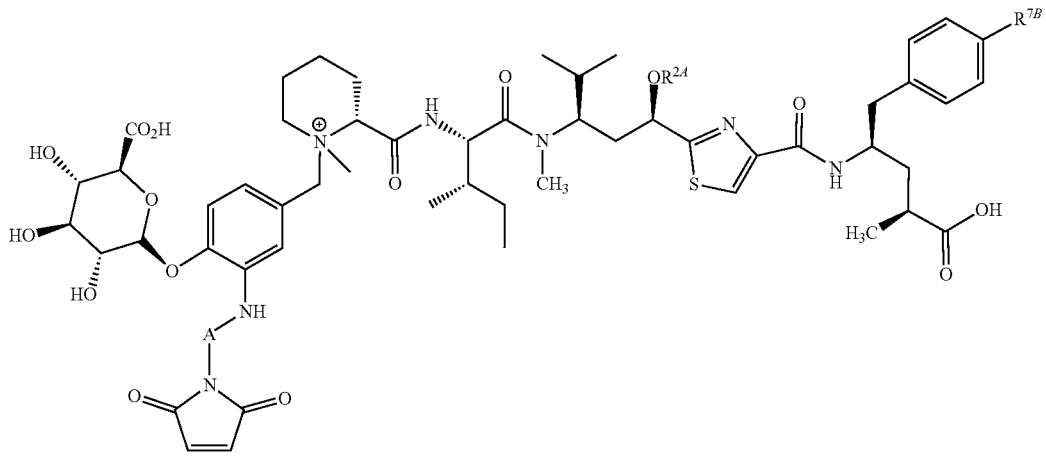

in salt form, in particular a pharmaceutically acceptable salt, wherein A is a Stretcher Unit; $R^{2A}$ is —C(=O)$R^{2B}$, wherein $R^{2B}$ is methyl, ethyl, propyl, iso-propyl, 2-methyl-prop-1-yl, 2,2-dimethyl-prop-1-yl, or vinyl, or $R^{2A}$ is methyl, ethyl, propyl, iso-propyl, prop-2-en-1-yl or 2-methyl-prop-2-en-1-yl and $R^{7B}$ is —H or —OH.

In more preferred embodiments the quaternized tubulysin drug unit is related to tubulysin M, which is also known as (αS,γR)-γ-[[[2-[(1R,3R)-1-(Acetyloxy)-4-methyl-3-[methyl[(2S,3S)-3-methyl-2-[[[(2R)-1-methyl-2-piperidinyl]carbonyl]-amino]-1-oxopentyl]amino]pentyl]-4-thiazolyl]carbonyl]amino]-α-methyl-benzenepentanoic acid and has CAS Number 936691-46-2. Therefore, more preferred glucuronide-based drug linker compounds having a quaternized tubulysin drug unit have the above structure in which $R^{2A}$ is —C(=O)CH$_3$ and $R^{7B}$ is hydrogen.

Accordingly particularly preferred glucuronide-based drug linker compounds for use in the present invention are as follows:

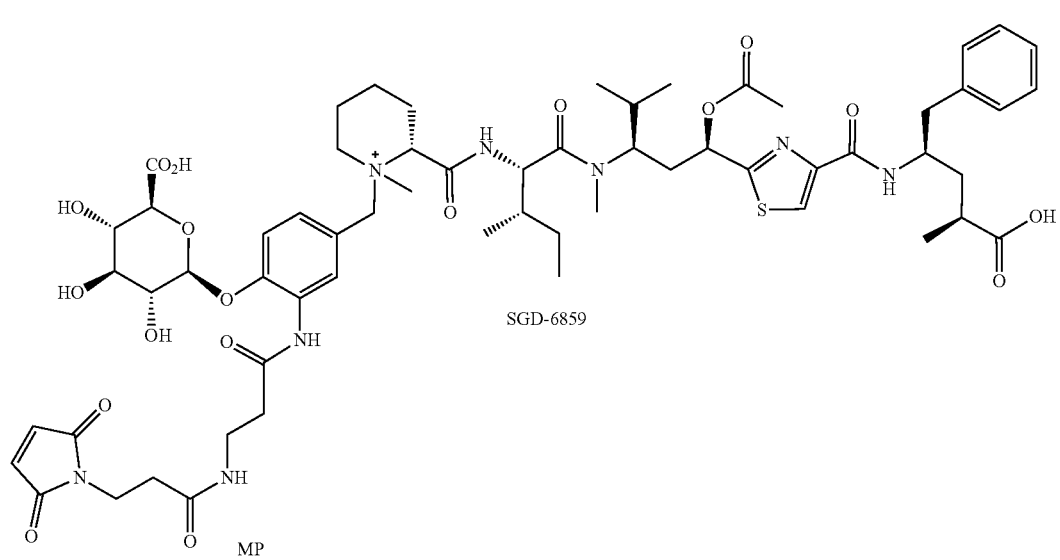

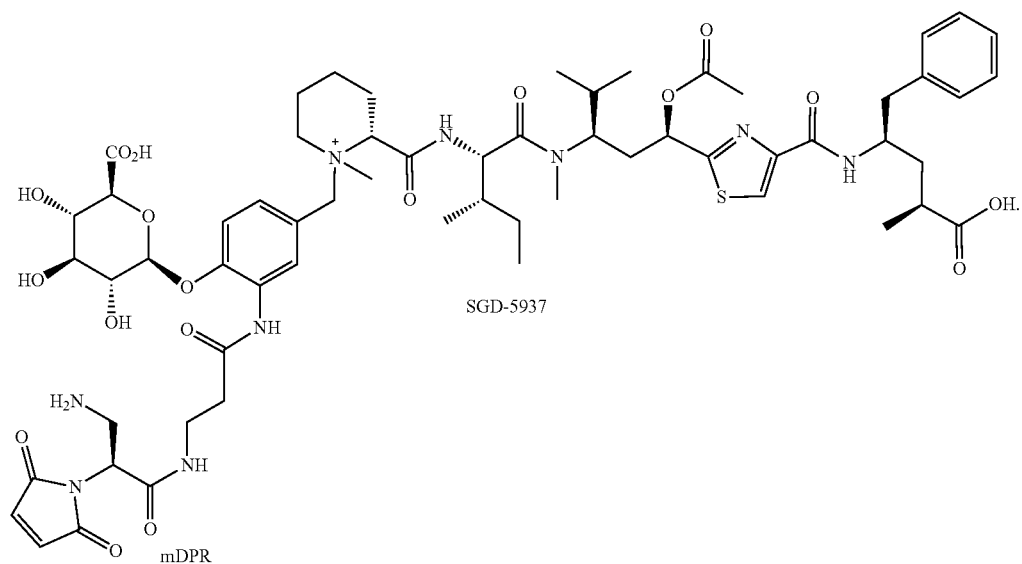

in salt form, in particular a pharmaceutically acceptable salt, wherein the amine nitrogen atom of the indicated mDPR moiety is preferably protonated or protected by a suitable acid-labile protecting group such as BOC. Other particularly preferred glucuronide-based drug linker compounds replace the tubuvaline N-methyl substituent with an ethyl or n-propyl substituent.

Other more preferred embodiments, the quaternized tubulysin drug unit are related to tubulysin M in which the O-linked acetate substituent of is tubuvaline moiety is replaced by an O-linked ethyl ether substituent (i.e., $R^{2A}$ is ethyl).

Accordingly, other particularly preferred glucuronide-based drug linker compounds for use in the present invention are as follows:

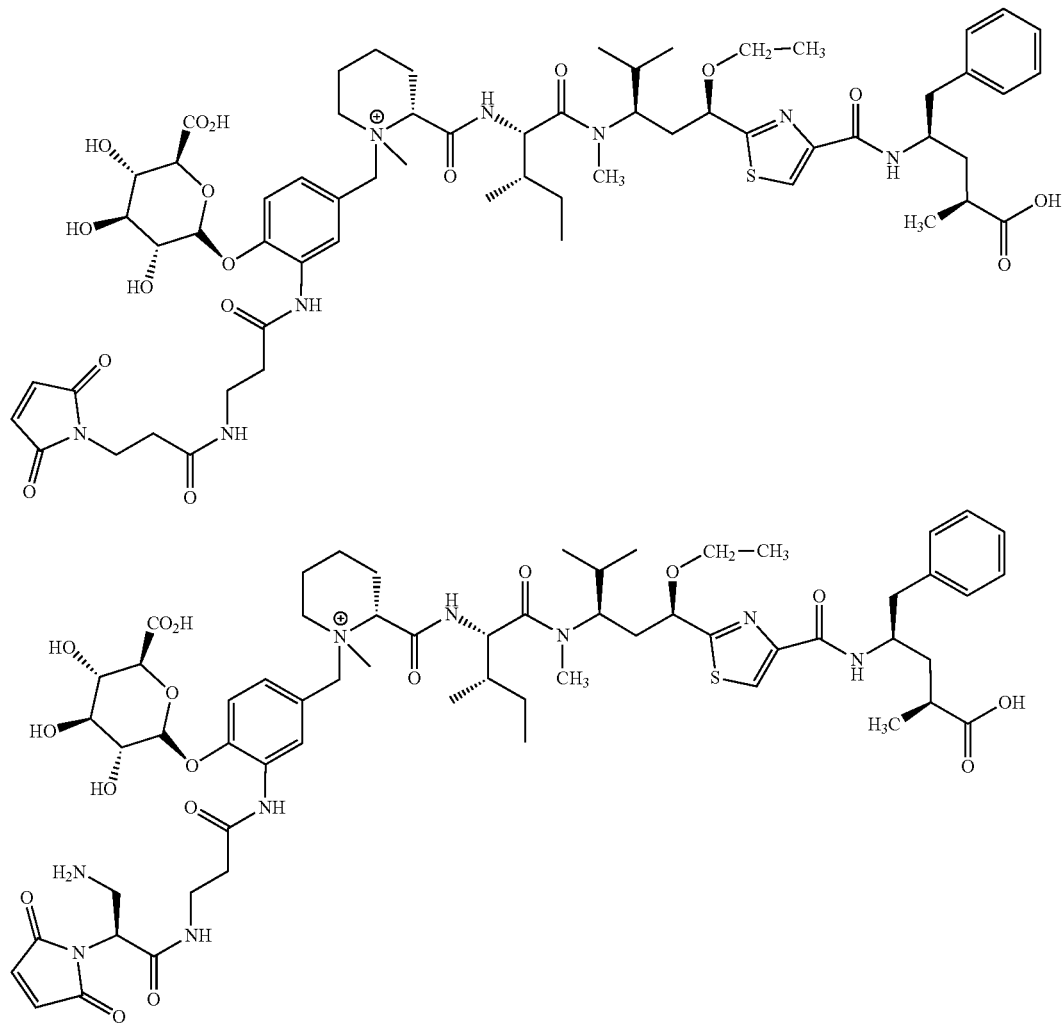

in salt form, in particular, a pharmaceutically acceptable salt.

Preparation of glucuronide-based tubulysin drug linker compounds are detailed in WO20160404684, and are specifically incorporated by reference herein. Those preparations are exemplified by the following reaction schemes:

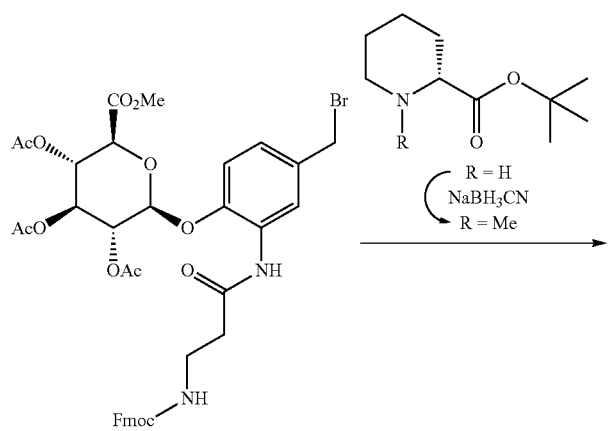

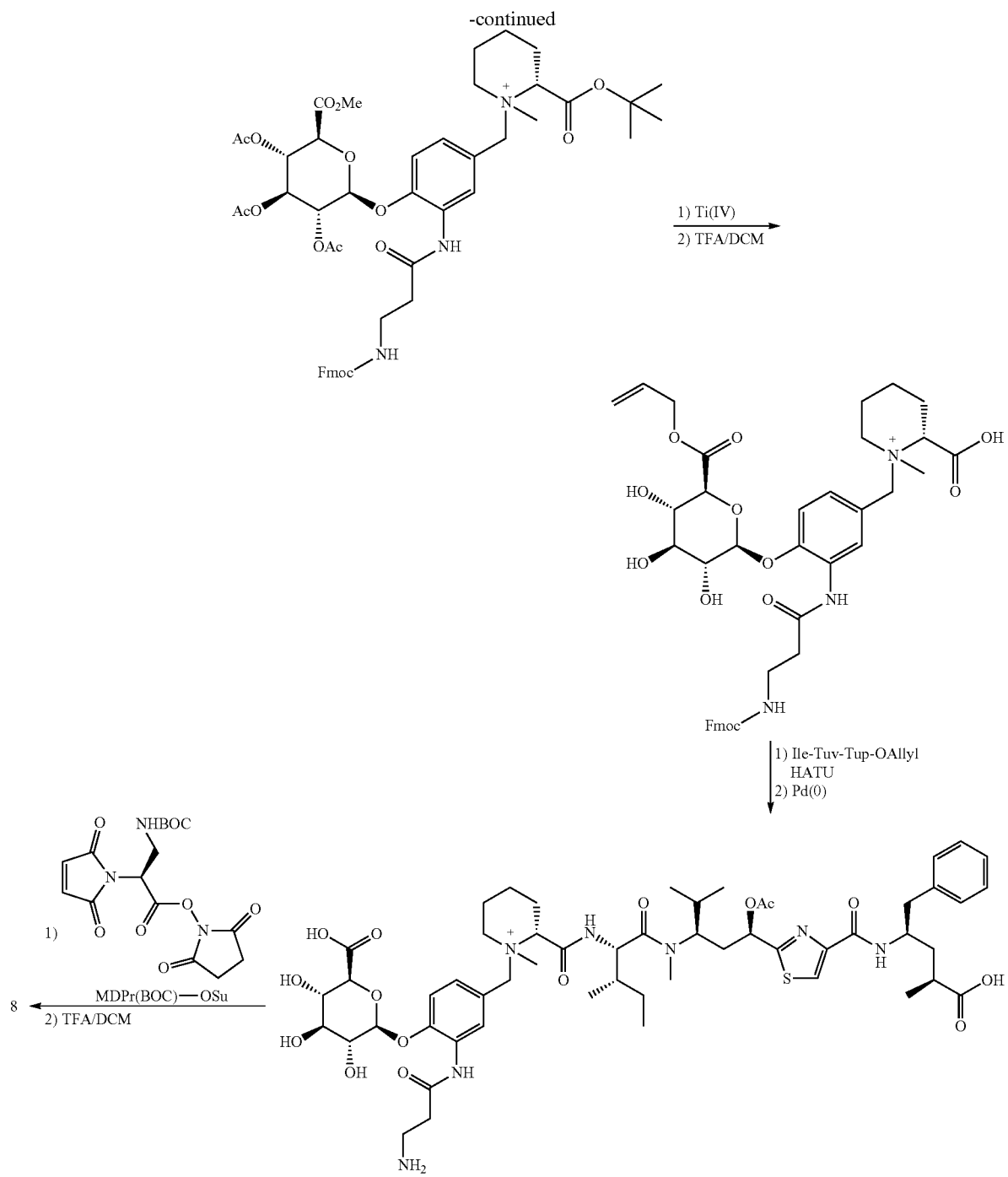

Preparation of mDPR(Boc)-OH, which is converted to its activated esters mDPR(BOC)-OSu and mDPR(BOC)-OPFF, is described in Nature Biotech, 2014, 32, 1059-1062), the procedure for which is specifically incorporated by reference herein, and preparation of the glucuronide intermediate, which is brominated for quaternization of tubulysin M, is described by Molecular Cancer Therapeutics, 2016, 15, 938-945, the procedure for which is specifically incorporated by reference herein.

An antibody drug conjugate of the present invention has the structure of any one of the above embodiments of a glucuronide-based drug linker compound in which cysteine variant residues at position 239 or 239/295 or 294 of an anti-GPC3 antibody has been condensed through Michael addition with the compound's maleimide moiety thereby converting that moiety to a succinimide moiety, which may then undergo hydrolysis at one of its carbonyl carbons.

Representative antibody drug conjugates of tubulysin M and analogs thereof in which the acetate group of the tubuvaline residue is replaced by an ether or another ester group that have attachment of a glucuronide linker to the tertiary amine nitrogen of the tubulysin Mep residue through quaternization of that nitrogen atom, and which may be prepared from drug linker compounds such as those described above, are exemplified as follows:

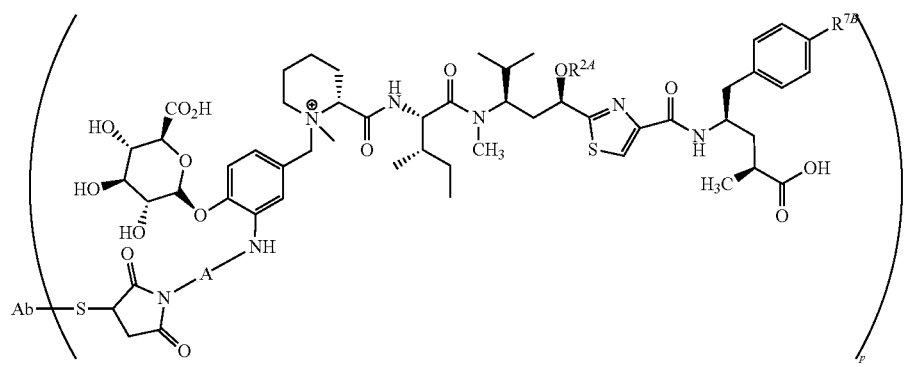

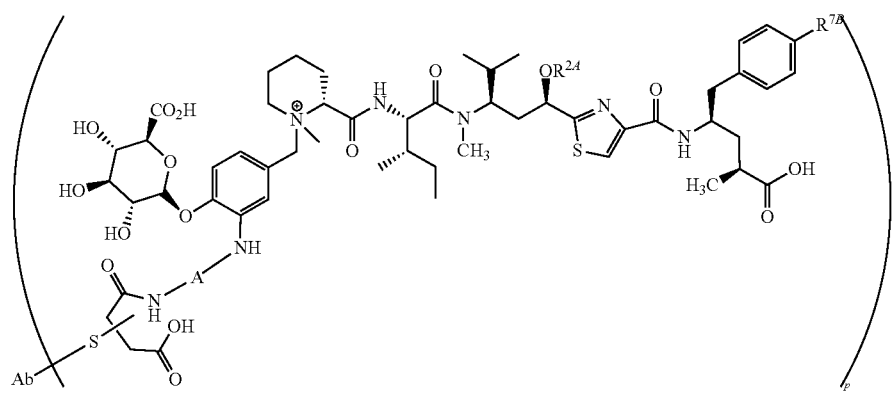

optionally in pharmaceutically acceptable salt form, wherein subscript p represents the drug loading and typically ranges from 1 to 4, and in some aspects is 2 or 4, Ab is an anti-GPC3 antibody and S is a sulfur atom from cysteine 239 or cysteine 295.

Antibodies or fusion proteins can also be conjugated via cysteine occupying position 239 or 295 to detectable markers such as an enzyme, a chromophore, or a fluorescent label. The latter ADC structure is related to the former by hydrolysis of the succinimide moiety at one of its carbonyl groups, and in some embodiments occurs when stretcher unit A is comprised of a basic unit.

Other exemplary GPC3 targeted antibody drug conjugates are shown below:

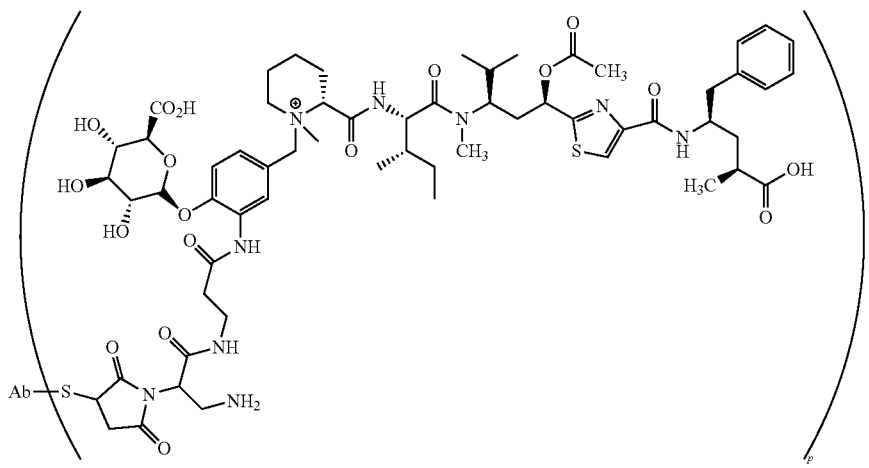

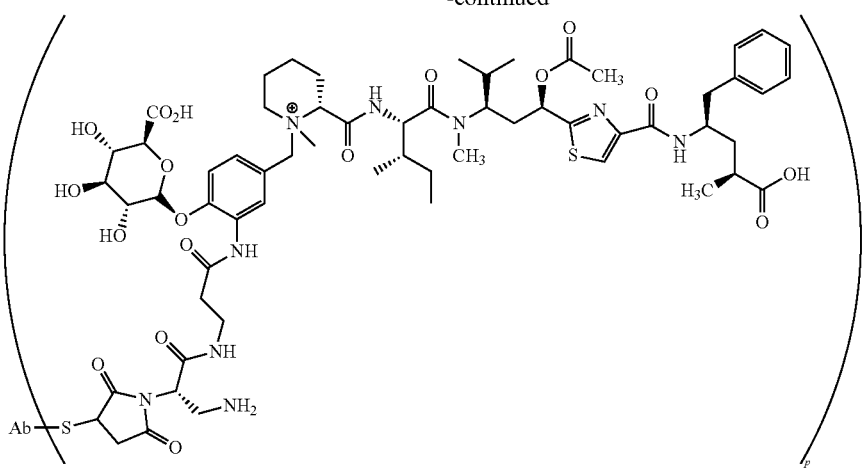
SGD-5937 ADC
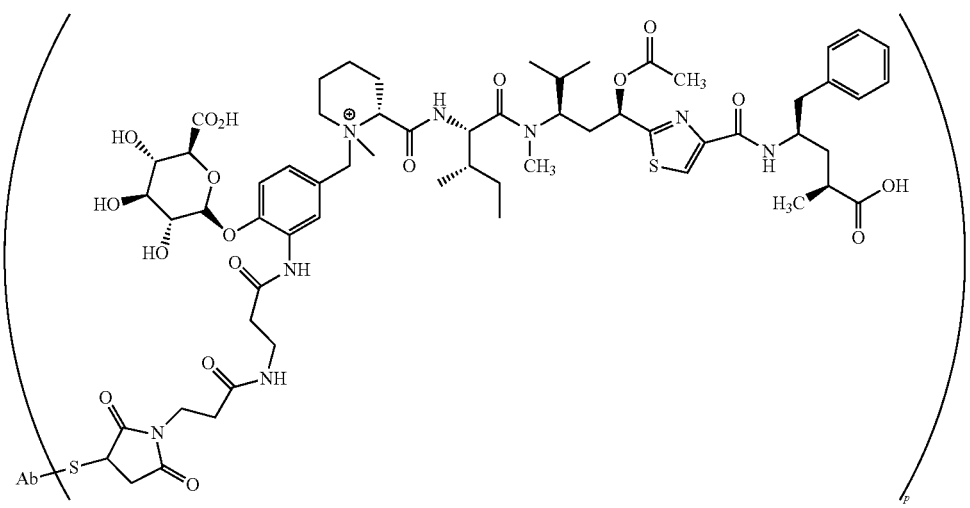
SGD-6859 ADC
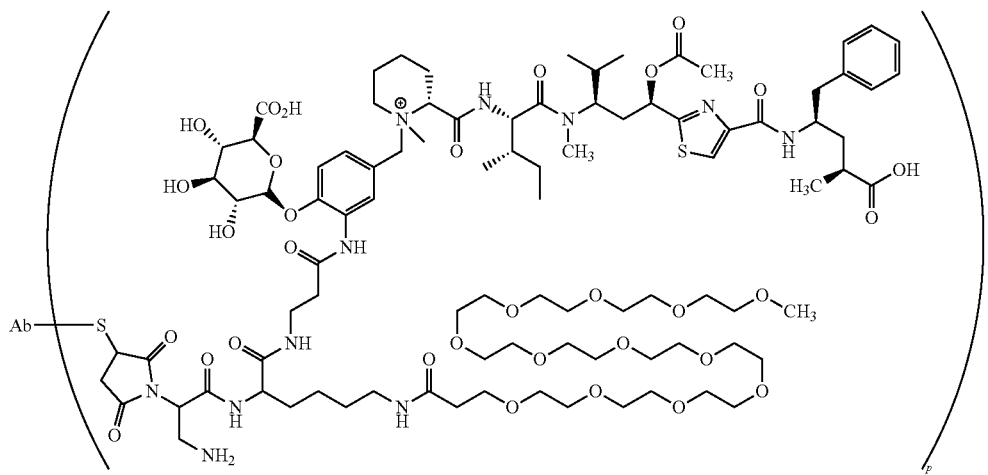

-continued

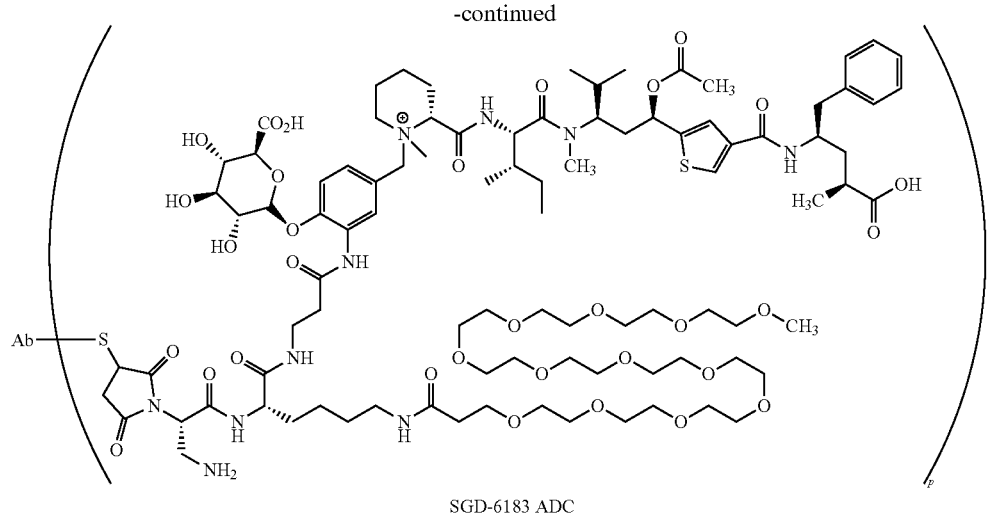

SGD-6183 ADC optionally in pharmaceutically acceptable salt form, wherein subscript p represents the drug loading and typically ranges from 1 to 4, and in some aspects is 2 or 4, Ab is an anti-GPC3 antibody and S is a sulfur atom from cysteine 239 or cysteine 295.

As well as being conjugated to a drug or label antibodies can also be linked via a cleavable linker attached to an inhibitory or masking domain that inhibits antibody binding (see, e.g., WO2003/068934, WO2004/009638, WO 2009/025846, WO2101/081173 and WO2014103973). The linker can be designed to be cleaved by enzymes that are specific to certain tissues or pathologies, thus enabling the antibody to be preferentially activated in desired locations. Masking moieties can act by binding directly to the binding site of an antibody or can act indirectly via steric hindrance.

Drug Loading—"p"

Referring to the GPC3 targeted antibody-drug conjugates shown above, the subscript p represents the drug load for an antibody molecule (number of molecules of drug attached to an antibody molecule) and is an integer value. In a composition comprising a population of antibody-drug conjugate molecules, the average drug load (e.g., the average number of drug-linker molecules per antibody in the population) is an important quality attribute as it determines the amount of drug that can be delivered to a target cell. The average drug load can be an integer or non-integer value but is typically a non-integer value. The optimal average drug load will vary depending on the identity of the drug or drug-linker combination.

The heterogeneity of an antibody-drug conjugate composition will, in some aspects, be dependent on the conjugation technology used to conjugate drug-linker molecules to antibody molecules. For example, in some aspects, the conjugation technology used to conjugate the drug-linker molecules to the antibody molecules will result in an antibody-drug conjugate composition that is heterogeneous with respect to the distribution of drug-linker molecules on the antibody and/or with respect to number of drug-linkers on the antibody molecules (e.g., when conjugating via interchain disulfides using non-site specific technology). In other aspects, the conjugation technology used to conjugate the drug-linker molecules will result in an antibody-drug conjugate composition that is substantially homogenous with respect to the distribution of drug-linker molecules on the ligand molecules and/or with respect to number of drug-linkers molecules on the antibody molecules (e.g., when using site specific conjugation technology). With both site specific and non-site specific methods, there will typically also be a small percentage of unconjugated antibody molecules. The percentage of unconjugated antibody molecules is included in the average drug load value.

In preferred aspects of the present invention, the average drug load when referring to a composition comprising a population of antibody-drug conjugate compounds is from about 2 to about 14, preferably about 2 to about 10. For the tubulysin M antibody drug conjugates exemplified herein, a particularly preferred average drug load is about 2. In some aspects, the actual drug load for individual antibody molecules in the population of antibody-drug conjugate compounds is from 1 to 4, 1 to 3 or 1 to 2 with a predominant drug loading of 2. In preferred aspects, the average drug load of about 2 is achieved via site specific conjugation techniques (e.g., engineered cysteines introduced to the antibody)

In some other aspects of the present invention, the average drug load when referring to a composition comprising a population of antibody-drug conjugate compounds is about 3 or about 4 and the actual drug load for individual antibody molecules in the population of antibody-drug conjugate compounds is from 1 to 8.

In some aspects, the actual drug load for individual antibody molecules in the population of antibody-drug conjugate compounds is from 1 to 10 (or from 6 to 10 or from 6 to 8). A higher drug load can be achieved, for example, if, in addition to the interchain disulfides, drug-linker is conjugated to introduced cysteine residues (such as a cysteine residue introduced at position 239, according to the EU index).

V. Therapeutic Applications

The GPC3 targeted antibody-drug conjugates described herein can be used to treat a GPC3 expressing disorder, such as GPC3 expressing cancer. Typically such cancers show detectable levels of GPC3 measured at the protein (e.g., by immunoassay) or RNA level. Some such cancers show elevated levels of GPC3 relative to noncancerous tissue of the same type, preferably from the same patient. Optionally, a level of GPC3 in a cancer is measured before performing treatment.

Examples of cancers associated with GPC3 expression include hepatocellular carcinoma (HCC) and lung carcinomas (GPC3 is expressed in approximately 70% of HCCs and 20% of lung carcinomas). Other cancers include Wilms tumor (nephroblastoma), ovarian clear cell carcinoma, colorectal carcinoma, and sarcomas.

Methods of the present invention include treating a patient that has a cancer that expresses GPC3 comprising administering to the patient an antibody-drug conjugate of the present invention. The cancer can be any GPC3 expressing cancer, including, for example, HCC, lung carcinoma, Wilms tumor, ovarian clear cell carcinoma, colorectal carcinoma, or sarcoma.

Some cancer cells develop resistance to a therapeutic agent after increasing expression of a protein increases efflux of the therapeutic agent out of the cancer cell. Such proteins include P-glycoprotein, multidrug resistance-associated protein, lung resistance-related protein, and breast cancer resistance protein. Detection of drug resistance in cancer cells can be performed by those of skill. Antibodies or assays that detect efflux proteins are commercially available from, e.g., Promega, Millipore, Abcam, and Sigma-Aldrich. The cancer to be treated by the present methods can be a multi-resistant cancer that expresses GPC3. In some aspects, the cancer will be a multi-drug resistant GPC3+ HCC.

GPC3 directed antibody-drug conjugates are administered in an effective regimen meaning a dosage, route of administration and frequency of administration that delays the onset, reduces the severity, inhibits further deterioration, and/or ameliorates at least one sign or symptom of cancer.

Exemplary dosages for GPC3 directed conjugates include from about 1.0 µg/kg to about 10 mg/kg, 1.0 µg/kg to about 5 mg/kg, 1.0 µg/kg to about 5 mg/kg, from about 1.0 µg/kg to about 1.0 mg/kg, from about 10 µg/kg to about 3 mg/kg, from about 10 µg/kg to about 2 mg/kg, from about 1.0 µg/kg to 1.0 mg/kg, or from about 1.0 µg/kg to 500.0 µg/kg or from about 1.0 µg/kg to 80.0, 100.0, or 200.0 µg/kg.

Exemplary dosages for GPC3 directed tubulysin M conjugates are generally from about 1.0 µg/kg to 1.0 mg/kg, or from about 1.0 µg/kg to 500.0 µg/kg or from about 1.0 µg/kg to 80.0, 100.0, or 200.0 µg/kg, although alternate dosages are contemplated.

Administration can be by a variety of administration routes. In certain embodiments, the conjugates are administered parenterally, such as intravenously, intramuscularly, or subcutaneously. For administration of an ADC for the treatment of cancer, the delivery can be into the systemic circulation by intravenous or subcutaneous administration. In a particular embodiment, administration is via intravenous delivery. Intravenous administration can be, for example, by infusion over a period such as 30-90 minutes or by a single bolus injection. In some aspects, administration will be via slow IV push (i.e., over 30-60 seconds) in a peripherally inserted central catheter.

The frequency of administration depends upon many different factors, including means of administration, target site, physiological state of the patient, whether the patient is human or an animal, and other medications administered. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are every three weeks or between once weekly or once monthly over a continuous course of treatment, although more or less frequent dosing is also possible. For subcutaneous administration, an exemplary dosing frequency is daily to monthly, although more or less frequent dosing is also possible.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, conjugates can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of conjugate in a liquid formulation can vary widely. In some aspects, the ADC is present at a concentration from about 0.5 mg/ml to about 30 mg/ml, from about 0.5 mg/ml to about 10 mg/ml, from about 1 mg/ml to about 10 mg/ml, from about 2 mg/ml to about 10 mg/ml, or from about 2 mg/ml to about 5 mg/ml.

Treatment with conjugates of the invention can be combined with chemotherapy, radiation, stem cell treatment, surgery, and other treatments effective against the disorder being treated, including standard of care for the particular disorder being treated. Accordingly, the present invention encompasses methods of treating the disease and disorders described herein as a monotherapy or in combination therapy with, for example, standard of care or investigational drugs for treatment of such diseases and/or disorders. Methods for the treatment of cancer include administering to a patient in need thereof an effective amount of a GPC3 directed antibody-drug conjugate of the present invention in combination with an additional anti-cancer agent or other agent to treat cancer.

Some agents for combination therapy include: sorafenib, regorafenib, nivolumab, doxorubicin, FEMOX (gemcitabine and oxaliplatin), doxorubin, cisplatin, carboplatin, docetaxel, gemcitabine, paclitaxel, pemetrexed, vinorelbine, and mitomycin C. In an embodiment, one or more of sorafenib, regorafenib, nivolumab, doxorubicin, FEMOX (gemcitabine and oxaliplatin), doxorubin, cisplatin, carboplatin, docetaxel, gemcitabine, paclitaxel, pemetrexed, vinorelbine, and mitomycin C is administered in a combination therapy with a GPC3 directed ADC of the present invention.

In a further embodiment, one or more of sorafenib, regorafenib, nivolumab, doxorubicin, FEMOX (gemcitabine and oxaliplatin), doxorubin, cisplatin, carboplatin, docetaxel, gemcitabine, paclitaxel, pemetrexed, vinorelbine, and mitomycin C is administered in a combination therapy with a humanized GPC3-1 ADC of the present invention. In a further embodiment, one or more of sorafenib, regorafenib, nivolumab, doxorubicin, FEMOX (gemcitabine and oxaliplatin), doxorubin, cisplatin, carboplatin, docetaxel, gemcitabine, paclitaxel, pemetrexed, vinorelbine, and mitomycin C is administered in a combination therapy with an hGPC3-1ec-SGD-6859 of the present invention.

Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Figure 6:
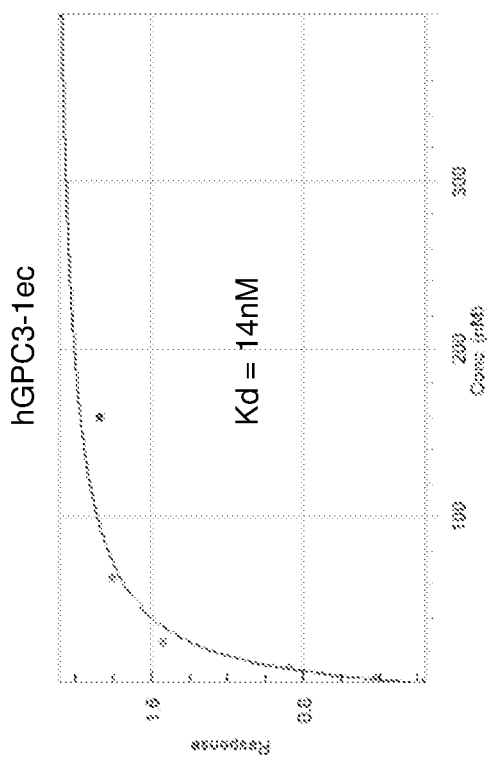
FIG. 6 shows surface plasmon resonance binding data for hGPC3-1ec. (Left) Multiple sensorgrams represent several concentrations (400, 160, 64, 25.6, 10.2, 4.1, and 1.64 nM) of hGPC3-1ec associating with immobilized hGPC3. (Right) The $K_D$ was determined by plotting the 600 second maximum response for each concentration and was defined by half maximal binding.
Figure 6:
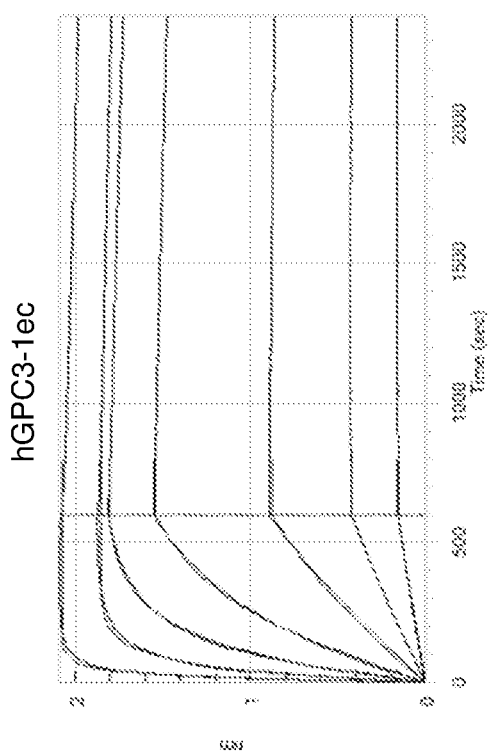

Cell lines described in the following examples were maintained in culture according to the conditions specified by the American Type Culture Collection (ATCC) or Deutsche Sammlung von Mikroorganismen and Zellkulturen GmbH, Braunschweig, Germany (DMSZ), or as otherwise known.
Methods
Antibody Selection The lead antibody, GPC3-1, was identified by immunizing mice with recombinant GPC3 encompassing amino acid residues 375-563 (see FIG. 1). Lymphocytes harvested from spleen and lymph nodes of GPC3 antibody producing mice were fused to myeloma cells. Fused cells were recovered overnight in hybridoma growth media. Following recovery, cells were spun down and then plated in semi-solid media. Hybridomas were incubated and IgG producing hybridoma clones were picked. Antibodies from this hybridoma campaign were screened as ADCs on GPC3 expressing cell lines. Antibodies from several epitope classes showed ADC activity. The lead antibody was selected based on its superior ADC cytotoxicity as well as having an epitope that is membrane proximal to the proteolytic cleavage site that can result in shedding
Competition Binding Assays One hundred thousand GPC3-positive cells were transferred to 96-well plates and incubated for 1 hour on ice with 3-5 nM AlexaFluor-488 labeled mGPC3-1 and increasing concentrations (from 10 pM to 2 uM) of unlabeled humanized or murine GPC3-1 mAb. Cells were centrifuged, washed 3 times with PBS, and resuspended in 125 μL of a PBS+2% FBS solution. Fluorescence was analyzed using a flow cytometer, and the percent of saturated fluorescent signal was used to determine percent labeled GPC3-1 mAb bound. The EC50 was extrapolated by fitting the data to a sigmoidal dose-response curve with variable slope.
Saturation Binding Assays One hundred thousand GPC3-positive cells were transferred to 96-well plates. AlexaFluor-488 labeled GPC3mAb was added in concentrations ranging from 10 pM to 5 uM and the cells incubated on ice for 30 minutes. Cells were pelleted by centrifugation, washed 3 times with a PBS+1% BSA solution, and resuspended in 125 μL of PBS+2% FBS. Fluorescence was analyzed using a flow cytometer, and the percent of saturated fluorescent signal was used to determine percent bound and to subsequently calculate apparent Kd.
Affinity Measured by Surface Plasmon Resonance Human GPC3 (hGPC3 GP3-H5258) was purchased from AcroBiosystems and biotinylated using Pierce NHS-LC-LC-Biotin at a molar ratio of 1.5:1 biotin/protein ratio. Biolayer interferometry (BLI) was performed on an Octet Red 384 system (ForteBio) with High Precision Streptavidin (SAX) Biosensors and GPC3 as the probe using hGPC3-1ec as the analyte. Bivalent binding to bound hGPC3 was measured to be 2.04E-10M (kdiss 2.3E-5/kon 1.134E5) with X2=0.59 and R2=0.9998 for an association of 600 sec and a disassociation of 1800 sec and fit at a 1:1 ratio over eight concentration points at 400, 160, 64, 25.6, 10.2, 4.1 and 1.64 nM. The binding affinity ($K_D$) of hGPC3-1ec (HBLE) was determined to be 14 nM (FIG. 6).

Design of Humanized Antibodies

Humanized antibodies were derived from the murine GPC3-1 antibody. Four humanized heavy chains (HA-HD) and seven humanized light chains (LA-LE) were made incorporating back mutations at different positions. In some instances, backmutations will match the murine germline, but in other cases it will not (as in the case with somatic mutations). Humanized heavy and light chains were paired. See, FIGS. 2-5 for the sequence alignments and Tables 1-5. After the initial humanization with HA, HB, HC, HD, and LA, LB, and LC variants, additional L-chain variants were developed to address the potential deamidation motif ("NG") found in CDR-L1 (SEQ ID NO: 13) (Table 5).

TABLE 1

Humanizing Mutations in hGPC3-1 Variable Heavy (vH) Chain Variants

| vH Variant | HV Exon Acceptor Sequence | Donor Framework Residues | Acceptor CDR Residues |
|---|---|---|---|
| hvHA | HV1-18/HJ4 | H48, H67, H69, H71 | None |
| hvHB | HV1-69-2/HJ4 | H69, H73, H93, H94 | None |
| hvHC | HV1-69-2/HJ4 | H24, H48, H67, H69, H73, H93, H94 | None |
| hvHD | HV1-69-2/HJ4 | H24, H38, H48, H66, H67, H69, H73, H93, H94 | None |

TABLE 2

Humanizing Mutations in hGPC3-1 Variable Light (vL) Chain Variants

| vL Variant | KV Exon Acceptor Sequence | Donor Framework Residues | Acceptor CDR Residues |
|---|---|---|---|
| hvLA | KV2-30/KJ2 | None | None |
| hvLB | KV2-30/KJ2 | L46 | None |
| hvLB-Q | KV2-30/KJ2 | L46 | None |
| hvLB-V | KV2-30/KJ2 | L46 | None |
| hvLC | KV2-30/KJ2 | L45, L46, L105, L106 | None |
| hvLD | KV2-30/KJ2 | L46 | L28 |
| hvLE | KV2-30/KJ2 | L46 | None |

TABLE 3

Specific Framework Mutations in hGPC3-1 Heavy Chain Variants

| Variant | 24 | 38 | 48 | 66 | 67 | 69 | 71 | 73 | 93 | 94 | % Human |
|---|---|---|---|---|---|---|---|---|---|---|---|
| hvHA | A | R | I* | R | A* | L* | A* | T | A | R | 83.7 |
| hvHB | V | Q | M | R | V | L* | A | K* | G* | R* | 88.5 |
| hvHC | A* | Q | I* | R | A* | L* | A | K* | G* | R* | 85.4 |
| hvHD | A* | K* | I* | K* | A* | L* | A | K* | G* | R* | 83.3 |

*Murine residues

TABLE 4

Specific Framework Mutations in hGPC3-1 Light Chain Variants

| Variant | 45 | 46 | 105 | 106 | % Human |
|---|---|---|---|---|---|
| hvLA | R | R | E | I | 92.0 |
| hvLB | R | L* | E | I | 91.0 |
| hvLB-Q | R | L* | E | I | 90.0 |
| hvLB-V | R | L* | E | I | 91.0 |
| hvLC | K* | L* | V* | M* | 90.0 |

TABLE 4-continued

Specific Framework Mutations in hGPC3-1 Light Chain Variants

| Variant | 45 | 46 | 105 | 106 | % Human |
|---|---|---|---|---|---|
| hvLD | R | L* | E | I | 92.0 |
| hvLE | R | L* | E | I | 90.0 |

*Murine residues

TABLE 5

Specific CDR-L1 Deamidation Mutations in hGPC3-1 Light Chain Variants

| Variant | 28 | 29 |
|---|---|---|
| hvLA | N | G |
| hvLB | N | G |
| hvLB-Q | Q | G |
| hvLB-V | N | V |
| hvLC | N | G |
| hvLD | D | G |
| hvLE | N | A |

Production of Antibody Drug Conjugates

Antibody drug conjugates were prepared as described in U.S. 62/465,129 (filed Feb. 28, 2017) and U.S. 62/561,151 (Sep. 20, 2017) using the anti-GPC3 antibodies described herein. Preparation of cysteine mutants of IgG1 mAb is generally described in US20100158909. The drug-linker SGD-6859 was conjugated to the anti-GPC3 antibody via a thiol group of a cysteine residue introduced at position 239 of the IgG1 chain of the antibody and the average drug load was about 2 drugs per antibody. Antibodies with cysteine at the 239 position carry the designation ec.

In Vitro Cytotoxicity Assay

Cell lines were plated 24 hours prior to antibody-drug conjugate (ADC) treatment. Cells were treated with the indicated doses of ADC and incubated for 96 hours at 37° C. In some experiments, non-antigen binding ADC was included as negative controls. Cell viability for the cell lines was measured using CelltiterGlo (Promega Corporation, Madison, WI) according to the manufacturer's instructions. Cells were incubated for 25 minutes at room temperature with the CelltiterGlo reagents and luminescence was measured on an Envision plate reader (Perkin Elmer, Waltham, MA). Results are reported as IC50, the concentration of compound needed to yield half maximal reduction in viability compared to vehicle-treated cells (control=100%).

In Vivo Activity Study

Subcutaneous HCC and Lung Carcinoma Models

Nude mice were inoculated subcutaneously with $5 \times 10^5$ JHH7 or $2.5 \times 10^6$ Hep3B or $2.5 \times 10^6$ Huh7 HCC cells. NSG mice were inoculated subcutaneously with $1 \times 10^6$ NCI-H661 cells. Tumor growth was monitored with calipers and the mean tumor volume was calculated using the formula ($0.5 \times$ [length $\times$ width$^2$]). When the mean tumor volume reached approximately 100 mm$^3$, mice were untreated or dosed intraperitoneally with a single dose of humanized GPC3-1 ADC. Mice were euthanized when tumor volumes reached approximately 400 mm$^3$. All animal procedures were performed under a protocol approved by the Institutional Animal Care and Use Committee in a facility accredited by the Association for Assessment and Accreditation of Laboratory Animal Care.

In Vivo Assessment of Maleimide and Tubulysin M Acetate Stability of SGD-5937 or SGD-6859 when Conjugate to S239C or Native Cysteines Drug stability as a function of drug-linker chemistry was assessed in SCID mice, the strain used in the xenograft models. Humanized IgG conjugates were prepared containing the MP glucuronide-tubulysin M (SGD-6859) and the mDPR glucuronide-tubulysin M (SGD-5937) loaded at 4-drugs/mAb on native cysteines and 2-drugs/mAb on engineered S239C. SCID mice were administered conjugate as a single ip dose of 3 mg/kg and then subjected to terminal bleeds at 4 and 10 days post-dose. Blood samples from each animal were processed to plasma using centrifugation into EDTA coated Eppendorf tubes. The plasma was batch purified using anti-human capture affinity resin (IgSelect, GE Healthcare) for three hours at 2-8° C. The bound samples were washed using PBS pH 7.4 (1×)+0.5 M NaCl and eluted using 50 mM glycine, pH 3. Eluted samples were neutralized with Tris pH 7.4 and deglycosylated using PNGase F (New England BioLabs Inc) then reduced using 10 mM DTT. Each sample was analyzed using reversed-phased UPLC (PLRP 8 um, Agilent) coupled with mass spectrometric detection (Waters Xevo G2-S QTOF). The drug-antibody ratio (DAR) of each sample was calculated using the relative ratios of total ion counts from the deconvoluted masses of the non-loaded and drug-loaded (acetylated and deacetylated) antibody peaks. Intact drug (% acetylation) was calculated using total ion counts of the drug loaded light chain and heavy chain species, assessed by a loss of 42 Daltons.

Results

Example 1: Design and Testing of Humanized mAbs

Several humanized GPC3-1 antibodies were constructed using the hIGHv1-18/hIGHJ4 or hIGHV1-69-2/hIGHJ4 heavy chain variable region human germlines and the hIGK2-30/hIGKJ2 light chain variable region human germlines as the human acceptor sequences. The antibodies differed in the selection of amino acid residues to be mutated back to the mouse antibody or mouse germline sequence. The antibody designated HBLE (heavy chain variable region as set forth in SEQ ID NO:1 (vHB) and the light chain variable region as set forth in SEQ I D NO:2 (vLE)) was selected as the lead humanized GPC3-1 antibody on the basis of its (i) binding characteristics (see Tables 6 and 7), (ii) ability to deliver drug and (iii) number of back mutations as compared to the other variants.

Antibodies designated HALA (antibody having the heavy chain variable region designated vHA and the light chain variable region designated vLA), HALB (antibody having the heavy chain variable region designated vHA and the light chain variable region designated vLB), HALC (antibody having the heavy chain variable region designated vHA and the light chain variable region designated vLC), HBLA (antibody having the heavy chain variable region designated vHB and the light chain variable region designated vLA), HBLB (antibody having the heavy chain variable region designated vHB and the light chain variable region designated vLB), HBLC (antibody having the heavy chain variable region designated vHB and the light chain variable region designated vLC), HBLD (antibody having the heavy chain variable region designated vHB and the light chain variable region designated vLD), HBLE (antibody having the heavy chain variable region designated vHB and the light chain variable region designated vLE), HBLB-Q (antibody having the heavy chain variable region designated vHB and the light chain variable region designated vLB-Q), HBLB-V (antibody having the heavy chain variable region designated vHB and the light chain variable region designated vLB-V), HCLA (antibody having the heavy chain variable region designated vHC and the light chain variable region designated vLA), HCLB (antibody having the heavy chain variable region designated vHC and the light chain variable region designated vLB), HCLC (antibody having the heavy chain variable region designated vHC and the light chain variable region designated vLC), HDLA (antibody having the heavy chain variable region designated vHD and the light chain variable region designated vLA), HDLB (antibody having the heavy chain variable region designated vHD and the light chain variable region designated vLB) and HDLC (antibody having the heavy chain variable region designated vHD and the light chain variable region designated vLC) can be used in the present invention in place of the HBLE antibody. See FIGS. 2-5 for the vHA, vHB, vHC, vHD, vLA, vLB, vLB-Q, vLB-V, vLC, vLD, and vLE sequences.

TABLE 6 hGPC3 Binding of hGPC3-1 Antibody Variants

|  | EC50 (nM) |
| --- | --- |
| mGPC3-1 | 9 |
| hGPC3-1 HALA | >300 |
| hGPC3-1 HALB | 91 |
| hGPC3-1 HALC | 63 |
| hGPC3-1 HBLA | 203 |
| hGPC3-1 HBLB | 14 |
| hGPC3-1 HBLC | 25 |
| hGPC3-1 HCLA | 76 |
| hGPC3-1 HCLB | 18 |
| hGPC3-1 HCLC | 19 |
| hGPC3-1 HDLA | 149 |
| hGPC3-1 HDLB | 10 |
| hGPC3-1 HDLC | 13 |

TABLE 7 hGPC3 Binding of hGPC3-1 Deamidation Variants

|  | EC50 (nM) |
| --- | --- |
| hGPC3-1 HBLB | 3 |
| hGPC3-1 HBLB-Q | 7 |
| hGPC3-1 HBLB-V | 4 |
| hGPC3-1 HBLD | 74 |
| hGPC3-1 HBLE | 3 |

Example 2: In Vitro Anti-Tumor Activity of hGPC3-1Ec SGD-6859/SGD-6183

Figure 7:
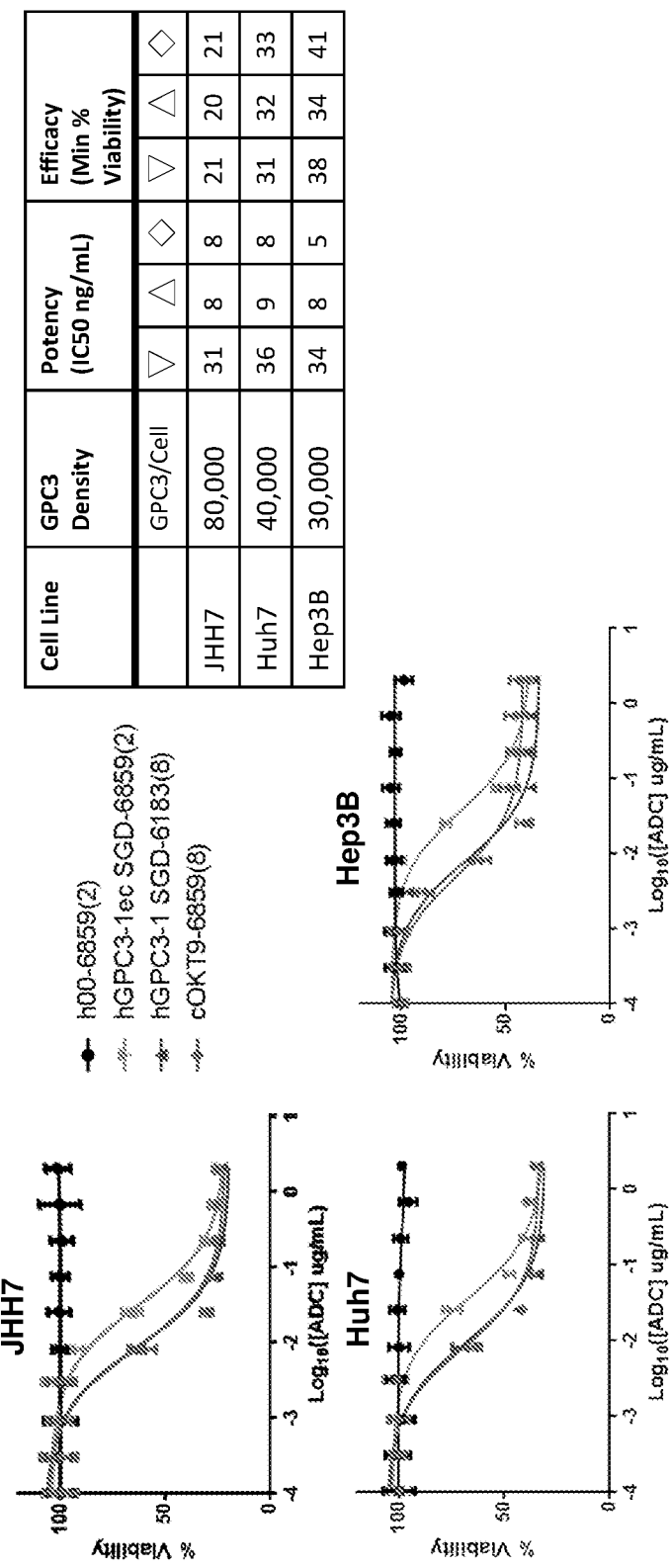
FIG. 7 shows the result of an in vitro cytotoxicity assay testing the humanized GPC3-1ec SGD-6859 or GPC3-1 SGD-6183 antibody-drug conjugate against a panel of GPC3 expressing HCC cell lines including JHH7, Huh7, and Hep3B.

The cytotoxic activity of humanized GPC3-1ec SGD-6859 or GPC3-1 SGD-6183 antibody-drug conjugates was evaluated against a panel of GPC3 expressing HCC cell lines including JHH7, Huh7, and Hep3B. As shown in FIG. 7, humanized GPC3-1ec SGD-6859 or GPC3-1 SGD-6183 antibody-drug conjugate were active in all three cell lines.

Figure 8:
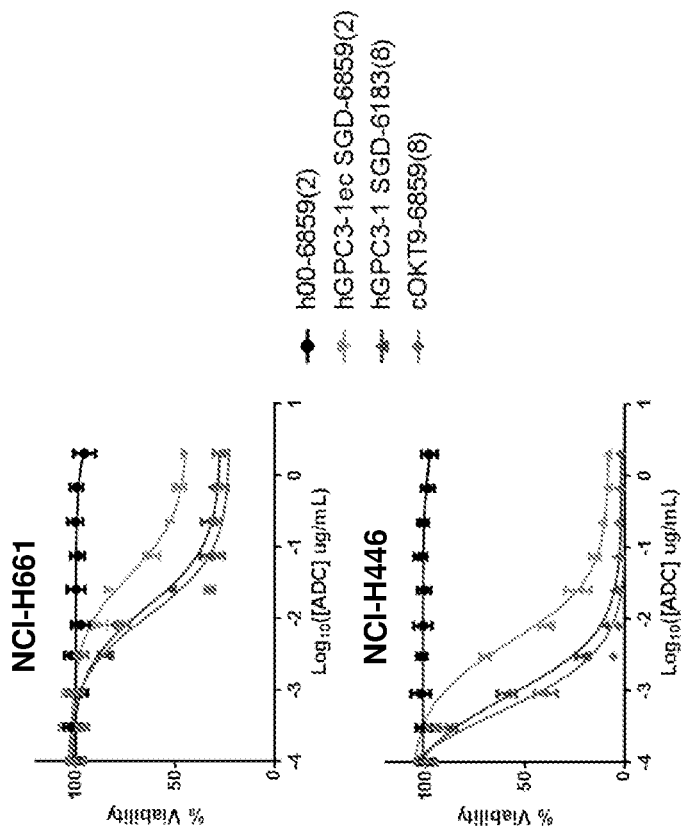
FIG. 8 shows the result of an in vitro cytotoxicity assay testing the humanized GPC3-1ec SGD-6859 or GPC3-1 SGD-6183 antibody-drug conjugate against a panel of GPC3 expressing lung carcinoma cell lines including NCI-H661 and NCI-H446.

The cytotoxic activity of humanized GPC3-1ec SGD-6859 or GPC3-1 SGD-6183 antibody-drug conjugate was evaluated against a panel of GPC3 expressing lung carcinoma cell lines including NCI-H661 and NCI-H446. As shown in FIG. 8, humanized GPC3-1ec SGD-6859 or GPC3-1 SGD-6183 antibody-drug conjugates were active in both cell lines.

Figure 9:
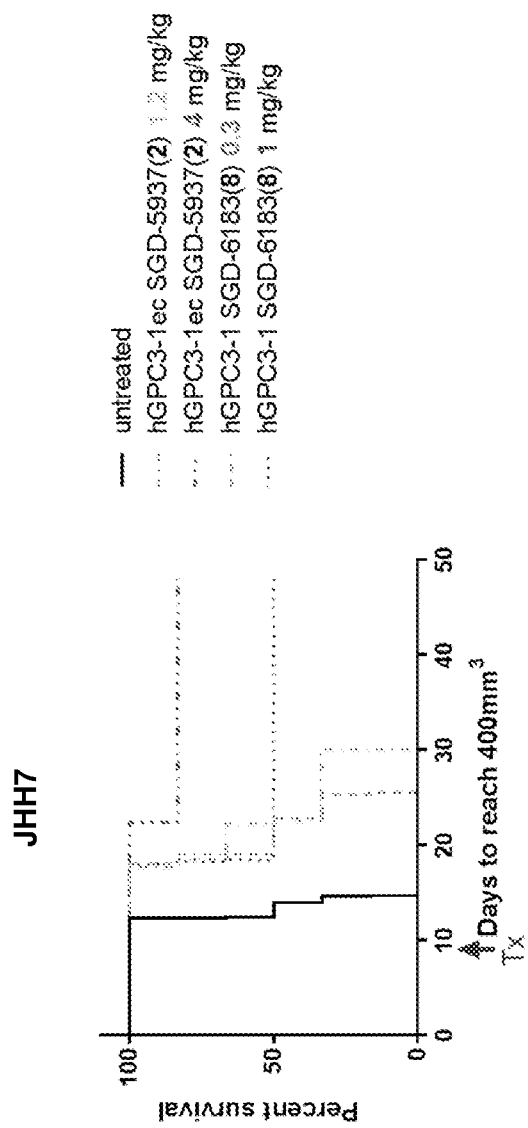
FIG. 9 shows the results of an HCC xenograft model, JHH7.
Figure 10:
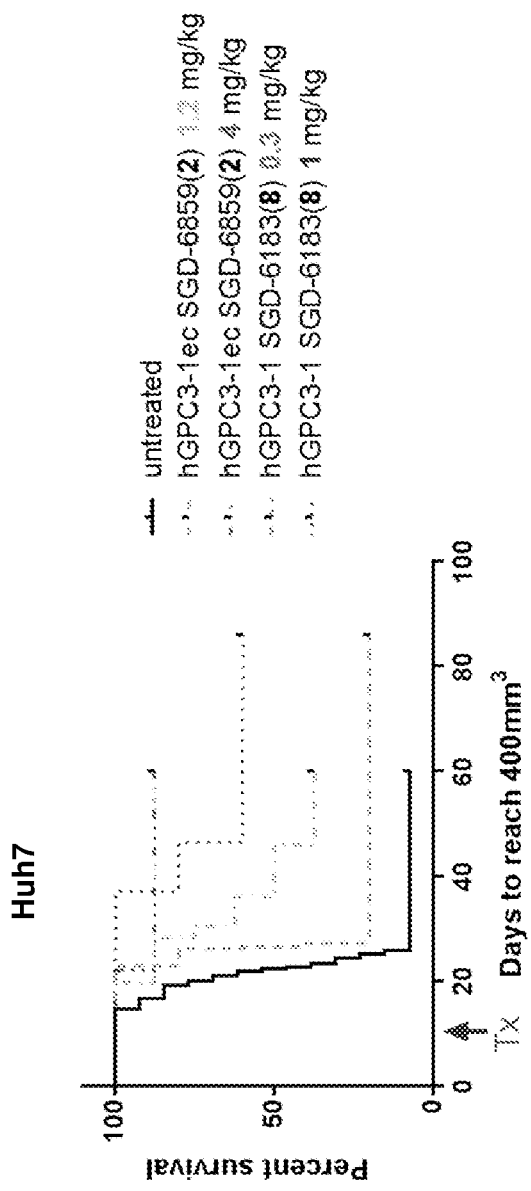
FIG. 10 shows the results of an HCC xenograft model, Huh7.
Figure 11:
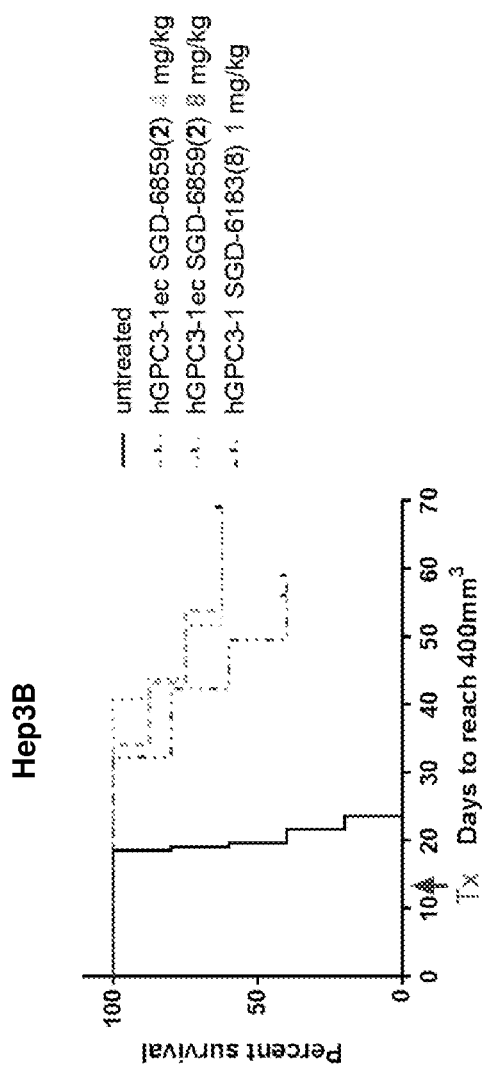
FIG. 11 shows the results of an HCC xenograft model, Hep3B.
Figure 12:
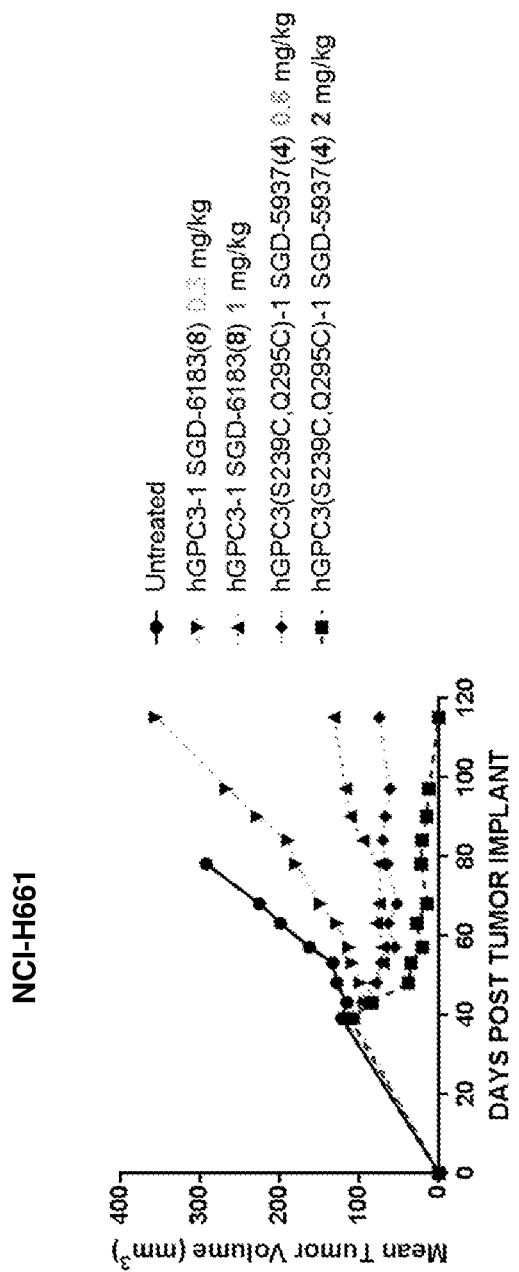
FIG. 12 shows the results of a lung carcinoma xenograft model, NCI-H661.

Example 3: In Vivo Anti-Tumor Activity of Humanized GPC3-1Ec SGD-6859 or GPC3-1(S239C, Q295C) SGD-5937 or GPC3-1 SGD-6183 on HCC Tumors The activity of hGPC3-1ec SGD-6859 or hGPC3-1ec SGD-5937 or hGPC3-1 SGD-6183 was tested in three subcutaneous HCC xenograft models, JHH7, Huh7, and Hep3B. Nude mice bearing established (~100 mm$^3$) tumors were dosed with hGPC3-1ecSGD-5937 or hGPC3-1 SGD-6183 as depicted in FIG. 9 for the JHH7 model, hGPC3-1ec SGD-6859 or hGPC3-1 SGD-6183 in FIG. 10 for the Huh7 tumor model, and hGPC3-1ec SGD-6859 or hGPC3-1 SGD-6183 in FIG. 11 for the Hep3B tumor model. Treatment with hGPC3-1ec SGD-6859 or hGPC3-1ecSGD-5937 or hGPC3-1 SGD-6183 decreased tumor growth compared to untreated. Durable regressions were obtained in several mice following a single ADC dose. The activity of hGPC3-1(S239C, Q295C) SGD-5937 or hGPC3-1 SGD-6183 was tested in one subcutaneous lung carcinoma xenograft model, NCI-H661. NSG mice bearing established (~100 mm$^3$) tumors were dosed with hGPC3-1(S239C, Q295C) SGD-5937 or hGPC3-1 SGD-6183 as depicted in FIG. 12. Treatment with hGPC3-1(S239C, Q295C) SGD-5937 or hGPC3-1 SGD-6183 decreased tumor growth compared to untreated. Durable regressions were obtained in several mice following a single ADC dose. The data demonstrate that hGPC3-1ec SGD-6859 or hGPC3-1ec SGD-5937 or hGPC3-1 SGD-6183 show significant dose-dependent anti-tumor activity in HCC xenograft models that express GPC3 and hGPC3-1(S239C, Q295C) SGD-5937 or hGPC3-1 SGD-6183 show significant dose-dependent anti-tumor activity in lung xenograft models that express GPC3.

Figure 13:
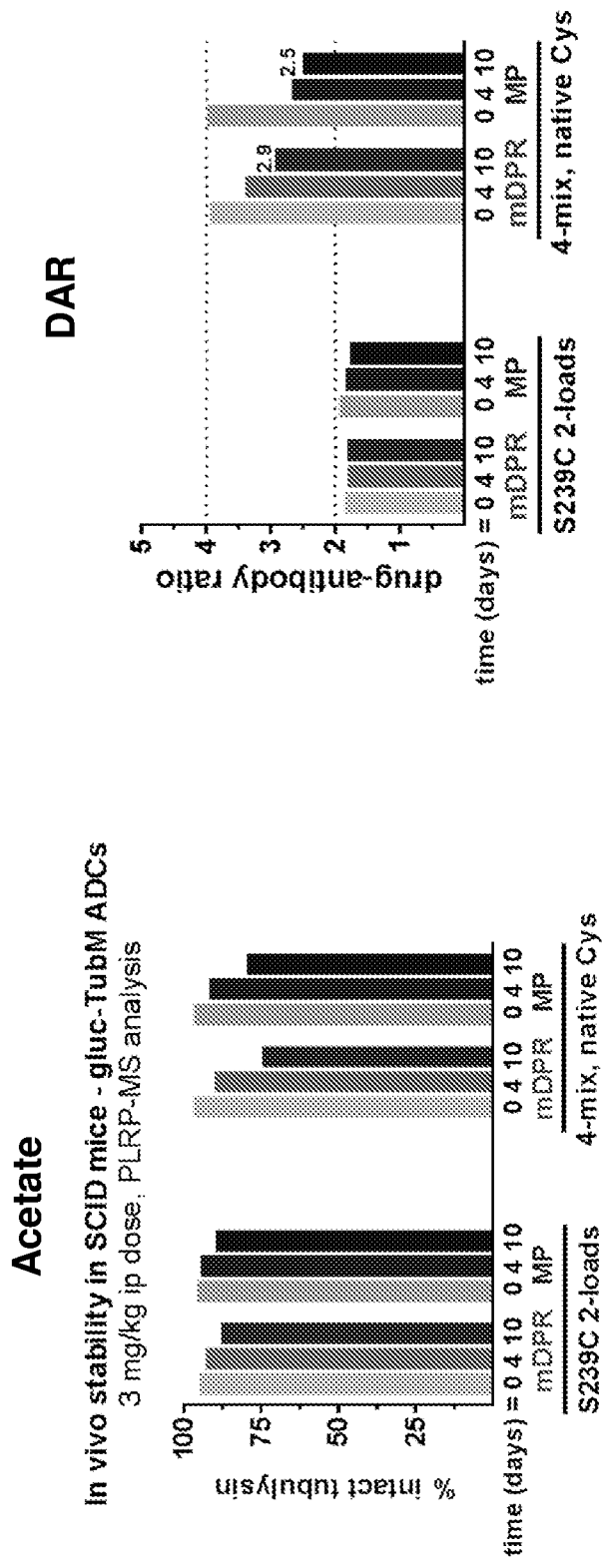
FIG. 13 shows the results of an in vivo assessment of tubulysin M acetate stability and linker maleimide stability when conjugated to S239C or native cysteines.

Example 4: In Vivo Assessment of Maleimide and Tubulysin M Acetate Stability of SGD-5937 or SGD-6859 when Conjugate to S239C or Native Cysteines Deacetylation of tubulysin M significantly decreases its potency. h00ec SGD-6859 or h00ec SGD-5937 were prepared as DAR 2 ADCs conjugated to S239C. h00 SGD-6859 or h00 SGD-5937 were prepared as mixed average DAR 4 ADCs conjugated to native cysteines. SCID mice were dosed intraperitoneally with 3 mg/kg of one of the ADCs. Maleimide stability and tubulysin M acetate stability was assessed at time 0, 4, and 10 days pot dose by PLRP-MS. Both SGD-6859 and SGD-5937 conjugated to native cysteines showed increased maleimide and tubulysin M instability when compared to conjugation to S239C (FIG. 13). This data shows that conjugation to S239C results in a more stable DAR and protection on the tubulysin M acetate critical for potency.

What is claimed is:

1. An antibody that specifically binds to the human Glypican-3 (GPC3) protein wherein the antibody comprises a heavy chain variable region comprising complementarity-determining regions (CDRs) comprising the amino acid sequences of the heavy chain variable region CDRs set forth in SEQ ID NO: 1, and a light chain variable region comprising CDRs comprising the amino acid sequences of the light chain variable region CDRs set forth in SEQ ID NO: 2.

2. The antibody of claim 1 that is a humanized, or chimeric antibody.

3. The antibody of claim 1, wherein the following variable region frameworks positions are occupied as specified: H24 is occupied by V or A, H38 is occupied by Q, R or K, H48 is occupied by M or I, H66 is occupied by R or K, H67 is occupied by V or A, H69 is occupied by L, H71 is occupied by A, H73 is occupied by K or T, H93 is occupied by G or A, H94 is occupied by R and the following amino acid residues of the light chain are present: L45 is occupied by R or K, L46 is occupied by L or R, L105 is occupied by E or V, L106 is occupied by I or M; numbering is via the Kabat numbering system.

4. The antibody of claim 1, wherein the following variable region frameworks positions are occupied as specified: H24 is occupied by V, H38 is occupied by Q, H48 is occupied by M, H66 is occupied by R, H67 is occupied by V, H69 is occupied by L, H71 is occupied by A, H73 is occupied by K, H93 is occupied by G, H94 is occupied by R; numbering is via the Kabat numbering system.

5. The antibody of claim 1, wherein the following variable region frameworks positions are occupied as specified: L45 is occupied by R, L46 is occupied by L, L105 is occupied by E, L106 is occupied by I; numbering is via the Kabat numbering system.

6. The antibody of claim 1 that is HALA, HALB, HALC, HBLA, HBLB, HBLC, HBLD, HBLE, HBLB-Q, HBLB-V, HCLA, HCLB, HCLC, HDLA, HDLB and HDLC.

7. The antibody of claim 1 wherein the heavy chain variable region is fused to a heavy chain constant region and the light chain variable region is fused to a light chain constant region.

8. The antibody of claim 7, wherein the heavy chain constant region is a mutant form of a natural human constant region which has reduced binding to an Fc gamma receptor relative to the natural human constant region.

9. The antibody of claim 7, wherein the heavy chain constant region is of IgG1 isotype.

10. The antibody of claim 7, wherein the heavy chain constant region has the amino acid sequence comprising SEQ ID NO:5 or SEQ ID NO:6 and the light chain constant region has the amino acid sequence comprising SEQ ID NO:7.

11. The antibody of claim 1, wherein the antibody is conjugated to a cytotoxic or cytostatic agent.

12. The antibody of claim 11 wherein the conjugated cytotoxic agent is a tubulysin.

13. The antibody of claim 11 wherein the conjugated cytotoxic agent is a conjugated tubulysin having the structure of:

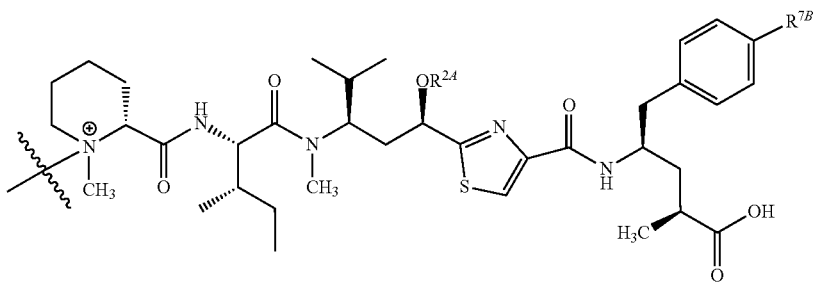

wherein the conjugated tubulysin is in salt form, in particular pharmaceutically acceptable salt form, or a solvate thereof, and wherein the wavy line indicates the site at which the tubulysin is conjugated to the antibody;

$R^{2A}$ is —C(=O)$R^{2B}$ wherein $R^{2B}$ is methyl, ethyl, propyl, iso-propyl, 2-methyl-prop-1-yl, 2,2-dimethyl-prop-1-yl, or vinyl, or $R^{2A}$ is methyl, ethyl, propyl, iso-propyl, prop-2-en-1-yl or 2-methyl-prop-2-en-1-yl; and $R^{7B}$ is —H or —OH.

14. The antibody of claim 11 wherein the conjugated cytotoxic agent is a conjugated tubulysin having the structure of:

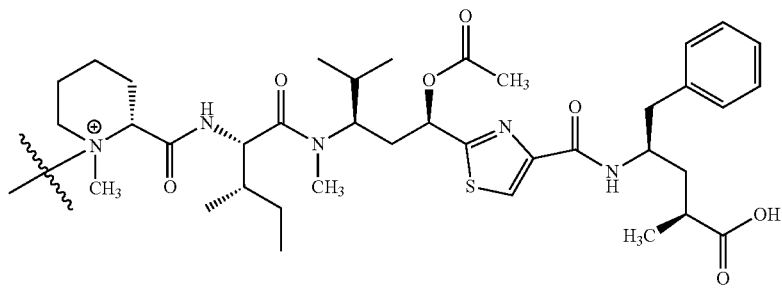

wherein the conjugated tubulysin is in salt from, in particular in pharmaceutically acceptable salt form, or a solvate thereof, and wherein the wavy line indicates the site at which the tubulysin is conjugated to the antibody.

15. The antibody of claim 11 wherein the conjugated cytotoxic agent is a conjugated tubulysin having the structure of:

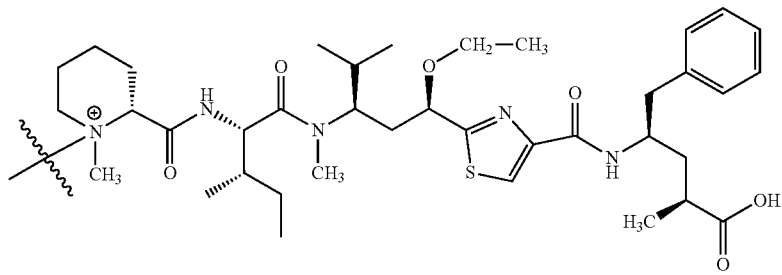

wherein the conjugated tubulysin is in salt form, in particular in pharmaceutically acceptable salt form, or a solvate thereof, and wherein the wavy line indicates the site at which the tubulysin is conjugated to the antibody.

16. A pharmaceutical composition comprising the antibody of claim 1; and a pharmaceutically acceptable carrier.

17. A method of treating a patient having a cancer that expresses GPC3, comprising administering to the patient an effective regimen of the composition of claim 16.

18. The method of claim 17, wherein the cancer is a hepatocellular carcinoma (HCC), a lung carcinoma, Wilms tumor (nephroblastoma), an ovarian clear cell carcinoma, a colorectal carcinoma, or a sarcoma.

19. The method of claim 17, wherein the cancer is HCC.

20. The antibody of claim 1, wherein the three heavy chain variable region CDRs are as set forth in SEQ ID NOs: 10, 11, and 12, and the three light chain variable region CDRs are as set forth in SEQ ID NOs: 13, 14, and 15.

21. The antibody of claim 1, wherein the heavy chain variable region comprises the sequence set forth in SEQ ID NO: 1, and the light chain variable region comprises the sequence set forth in SEQ ID NO: 2.

* * * * *

SEQUENCE LISTING

<160> NUMBER OF SEQ ID NOS: 30

<210> SEQ ID NO 1
<211> LENGTH: 115
<212> TYPE: PRT
<213> ORGANISM: Artificial Sequence
<220> FEATURE:
<223> OTHER INFORMATION: Heavy chain variable region for HB

<400> SEQUENCE: 1

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Glu Met His Trp Val Gln Ala Pro Gly Lys Gly Leu Glu Trp Met
        35                  40                  45

Gly Gly Ile Asp Pro Glu Thr Gly Gly Thr Ala Tyr Asn Gln Lys Phe
    50                  55                  60

Lys Gly Arg Val Thr Leu Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Gly Arg Tyr Tyr Ser Phe Ala Tyr Trp Gly Gln Gly Thr Leu Val Thr
            100                 105                 110

Val Ser Ser
        115
```

<210> SEQ ID NO 2
<211> LENGTH: 112
<212> TYPE: PRT
<213> ORGANISM: Artificial Sequence
<220> FEATURE:
<223> OTHER INFORMATION: Light chain variable region for LE

<400> SEQUENCE: 2

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Gln Trp Phe Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Ser His Val Pro Tyr Thr Phe Gly Gln Gly Thr Lys Leu Glu Ile Lys
            100                 105                 110
```

<210> SEQ ID NO 3
<211> LENGTH: 445
<212> TYPE: PRT
<213> ORGANISM: Artificial Sequence
<220> FEATURE:
<223> OTHER INFORMATION: Heavy chain for HB with mutant IgG1

<400> SEQUENCE: 3

```
Glu Val Gln Leu Val Gln Ser Gly Ala Glu Val Lys Lys Pro Gly Ala
1               5                   10                  15
```

```
Thr Val Lys Ile Ser Cys Lys Val Ser Gly Tyr Phe Thr Asp Tyr
            20                  25                  30

Glu Met His Trp Val Gln Gln Ala Pro Gly Lys Gly Leu Glu Trp Met
        35                  40                  45

Gly Gly Ile Asp Pro Glu Thr Gly Gly Thr Ala Tyr Asn Gln Lys Phe
50                  55                  60

Lys Gly Arg Val Thr Leu Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Gly Arg Tyr Tyr Ser Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
            210                 215                 220

Pro Pro Cys Pro Ala Pro Glu Leu Leu Gly Gly Pro Cys Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430
```

His Tyr Thr Gln Lys Ser Leu Ser Leu Ser Pro Gly Lys
            435                 440                 445

<210> SEQ ID NO 4
<211> LENGTH: 219
<212> TYPE: PRT
<213> ORGANISM: Artificial Sequence
<220> FEATURE:
<223> OTHER INFORMATION: Light chain for LE

<400> SEQUENCE: 4

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Gln Trp Phe Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Ser His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 5
<211> LENGTH: 330
<212> TYPE: PRT
<213> ORGANISM: Artificial Sequence
<220> FEATURE:
<223> OTHER INFORMATION: mutant heavy chain constant region

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 330
<212> TYPE: PRT
<213> ORGANISM: Artificial Sequence
<220> FEATURE:
<223> OTHER INFORMATION: Naturally occurring heavy chain constant region

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 7
<211> LENGTH: 107
<212> TYPE: PRT
<213> ORGANISM: Artificial Sequence
<220> FEATURE:
<223> OTHER INFORMATION: Light chain constant region

<400> SEQUENCE: 7

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 8
<211> LENGTH: 115
<212> TYPE: PRT
<213> ORGANISM: Artificial Sequence
```

```
<220> FEATURE:
<223> OTHER INFORMATION: murine GPC3-1 antibody heavy chain variable
      region

<400> SEQUENCE: 8

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
                20                  25                  30

Glu Met His Trp Val Lys Gln Thr Pro Val His Gly Leu Glu Trp Ile
            35                  40                  45

Gly Gly Ile Asp Pro Glu Thr Gly Gly Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Gly Arg Tyr Tyr Ser Phe Ala Tyr Trp Gly Gln Gly Thr Leu Val Thr
            100                 105                 110

Val Ser Ala
        115

<210> SEQ ID NO 9
<211> LENGTH: 112
<212> TYPE: PRT
<213> ORGANISM: Artificial Sequence
<220> FEATURE:
<223> OTHER INFORMATION: murine GPC3-1 antibody light chain variable
      region

<400> SEQUENCE: 9

Asp Val Leu Met Thr Gln Thr Pro Leu Ser Leu Pro Leu Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Gln Trp Phe Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Gly Arg Val Glu Ala Glu Asp Leu Gly Val Tyr Tyr Cys Phe Gln Val
                85                  90                  95

Ser His Val Pro Tyr Thr Phe Gly Gly Gly Thr Lys Leu Val Met Lys
            100                 105                 110

<210> SEQ ID NO 10
<211> LENGTH: 5
<212> TYPE: PRT
<213> ORGANISM: Artificial Sequence
<220> FEATURE:
<223> OTHER INFORMATION: amino acid sequence of CDR-H1 of humanized
      GPC3-1

<400> SEQUENCE: 10

Asp Tyr Glu Met His
1               5

<210> SEQ ID NO 11
<211> LENGTH: 20
```

```
<212> TYPE: PRT
<213> ORGANISM: Artificial Sequence
<220> FEATURE:
<223> OTHER INFORMATION: amino acid sequence of CDR-H2 of humanized
      GPC3-1

<400> SEQUENCE: 11

Trp Ile Gly Gly Ile Asp Pro Glu Thr Gly Gly Thr Ala Tyr Asn Gln
1               5                   10                  15

Lys Phe Lys Gly
            20

<210> SEQ ID NO 12
<211> LENGTH: 6
<212> TYPE: PRT
<213> ORGANISM: Artificial Sequence
<220> FEATURE:
<223> OTHER INFORMATION: amino acid sequence of CDR-H3 of humanized
      GPC3-1

<400> SEQUENCE: 12

Tyr Tyr Ser Phe Ala Tyr
1               5

<210> SEQ ID NO 13
<211> LENGTH: 16
<212> TYPE: PRT
<213> ORGANISM: Artificial Sequence
<220> FEATURE:
<223> OTHER INFORMATION: amino acid sequence of CDR-L1 of humanized
      GPC3-1

<400> SEQUENCE: 13

Arg Ser Ser Gln Ser Ile Val His Ser Asn Gly Asn Thr Tyr Leu Gln
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: amino acid sequence of CDR-L2 of humanized
      GPC3-1

<400> SEQUENCE: 14

Lys Val Ser Asn Arg Phe Ser
1               5

<210> SEQ ID NO 15
<211> LENGTH: 9
<212> TYPE: PRT
<213> ORGANISM: Artificial Sequence
<220> FEATURE:
<223> OTHER INFORMATION: amino acid sequence of CDR-L3 of humanized
      GPC3-1

<400> SEQUENCE: 15

Phe Gln Val Ser His Val Pro Tyr Thr
1               5

<210> SEQ ID NO 16
<211> LENGTH: 115
<212> TYPE: PRT
<213> ORGANISM: Artificial Sequence
<220> FEATURE:
<223> OTHER INFORMATION: GPC3-1 hvHA

<400> SEQUENCE: 16
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Ile
        35                  40                  45

Gly Gly Ile Asp Pro Glu Thr Gly Thr Ala Tyr Asn Gln Lys Phe
    50                  55                  60

Lys Gly Arg Ala Thr Leu Thr Ala Asp Thr Ser Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Tyr Tyr Ser Phe Ala Tyr Trp Gly Gln Gly Thr Leu Val Thr
            100                 105                 110

Val Ser Ser
        115

<210> SEQ ID NO 17
<211> LENGTH: 115
<212> TYPE: PRT
<213> ORGANISM: Artificial Sequence
<220> FEATURE:
<223> OTHER INFORMATION: GPC3-1 hvHC

<400> SEQUENCE: 17

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Thr Asp Tyr
            20                  25                  30

Glu Met His Trp Val Gln Gln Ala Pro Gly Lys Gly Leu Glu Trp Ile
        35                  40                  45

Gly Gly Ile Asp Pro Glu Thr Gly Thr Ala Tyr Asn Gln Lys Phe
    50                  55                  60

Lys Gly Arg Ala Thr Leu Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Gly Arg Tyr Tyr Ser Phe Ala Tyr Trp Gly Gln Gly Thr Leu Val Thr
            100                 105                 110

Val Ser Ser
        115

<210> SEQ ID NO 18
<211> LENGTH: 115
<212> TYPE: PRT
<213> ORGANISM: Artificial Sequence
<220> FEATURE:
<223> OTHER INFORMATION: GPC3-1 hvHD

<400> SEQUENCE: 18

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Thr Asp Tyr
            20                  25                  30

Glu Met His Trp Val Lys Gln Ala Pro Gly Lys Gly Leu Glu Trp Ile
        35                  40                  45

Gly Gly Ile Asp Pro Glu Thr Gly Gly Thr Ala Tyr Asn Gln Lys Phe

```
                    50                  55                  60
Lys Gly Lys Ala Thr Leu Thr Ala Asp Lys Ser Thr Asp Thr Ala Tyr
 65                  70                  75                  80

Met Glu Leu Ser Ser Leu Arg Ser Glu Asp Thr Ala Val Tyr Tyr Cys
                     85                  90                  95

Gly Arg Tyr Tyr Ser Phe Ala Tyr Trp Gly Gln Gly Thr Leu Val Thr
                100                 105                 110

Val Ser Ser
        115
```

<210> SEQ ID NO 19
<211> LENGTH: 112
<212> TYPE: PRT
<213> ORGANISM: Artificial Sequence
<220> FEATURE:
<223> OTHER INFORMATION: GPC3-1 hvLA

<400> SEQUENCE: 19

```
Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Ile Val His Ser
                 20                  25                  30

Asn Gly Asn Thr Tyr Leu Gln Trp Phe Gln Gln Arg Pro Gly Gln Ser
             35                  40                  45

Pro Arg Arg Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Val
                 85                  90                  95

Ser His Val Pro Tyr Thr Phe Gly Gln Gly Thr Lys Leu Glu Ile Lys
                100                 105                 110
```

<210> SEQ ID NO 20
<211> LENGTH: 112
<212> TYPE: PRT
<213> ORGANISM: Artificial Sequence
<220> FEATURE:
<223> OTHER INFORMATION: GPC3-1 hvLB

<400> SEQUENCE: 20

```
Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Ile Val His Ser
                 20                  25                  30

Asn Gly Asn Thr Tyr Leu Gln Trp Phe Gln Gln Arg Pro Gly Gln Ser
             35                  40                  45

Pro Arg Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Val
                 85                  90                  95

Ser His Val Pro Tyr Thr Phe Gly Gln Gly Thr Lys Leu Glu Ile Lys
                100                 105                 110
```

<210> SEQ ID NO 21
<211> LENGTH: 112

```
<212> TYPE: PRT
<213> ORGANISM: Artificial Sequence
<220> FEATURE:
<223> OTHER INFORMATION: GPC3-1 hvLB-Q

<400> SEQUENCE: 21

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Gln Gly Asn Thr Tyr Leu Gln Trp Phe Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Ser His Val Pro Tyr Thr Phe Gly Gln Gly Thr Lys Leu Glu Ile Lys
            100                 105                 110

<210> SEQ ID NO 22
<211> LENGTH: 112
<212> TYPE: PRT
<213> ORGANISM: Artificial Sequence
<220> FEATURE:
<223> OTHER INFORMATION: GPC3-1 hvLB-V

<400> SEQUENCE: 22

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Val Asn Thr Tyr Leu Gln Trp Phe Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Ser His Val Pro Tyr Thr Phe Gly Gln Gly Thr Lys Leu Glu Ile Lys
            100                 105                 110

<210> SEQ ID NO 23
<211> LENGTH: 112
<212> TYPE: PRT
<213> ORGANISM: Artificial Sequence
<220> FEATURE:
<223> OTHER INFORMATION: GPC3-1 hvLC

<400> SEQUENCE: 23

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Gln Trp Phe Gln Gln Arg Pro Gly Gln Ser
        35                  40                  45

Pro Lys Leu Leu Ile Tyr Lys Val Ser Asn Arg Phe Ser Gly Val Pro
```

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Val
                    85                  90                  95

Ser His Val Pro Tyr Thr Phe Gly Gln Gly Thr Lys Leu Val Met Lys
                   100                 105                 110

<210> SEQ ID NO 24
<211> LENGTH: 112
<212> TYPE: PRT
<213> ORGANISM: Artificial Sequence
<220> FEATURE:
<223> OTHER INFORMATION: GPC3-1 hvLD

<400> SEQUENCE: 24

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Ile Val His Ser
                 20                  25                  30

Asp Gly Asn Thr Tyr Leu Gln Trp Phe Gln Gln Arg Pro Gly Gln Ser
             35                  40                  45

Pro Arg Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Val
                    85                  90                  95

Ser His Val Pro Tyr Thr Phe Gly Gln Gly Thr Lys Leu Glu Ile Lys
                   100                 105                 110

<210> SEQ ID NO 25
<211> LENGTH: 98
<212> TYPE: PRT
<213> ORGANISM: Artificial Sequence
<220> FEATURE:
<223> OTHER INFORMATION: Mu IGHV1-15

<400> SEQUENCE: 25

Gln Val Gln Leu Gln Gln Ser Gly Ala Glu Leu Val Arg Pro Gly Ala
  1               5                  10                  15

Ser Val Thr Leu Ser Cys Lys Ala Ser Gly Tyr Thr Phe Thr Asp Tyr
                 20                  25                  30

Glu Met His Trp Val Lys Gln Thr Pro Val His Gly Leu Glu Trp Ile
             35                  40                  45

Gly Ala Ile Asp Pro Glu Thr Gly Gly Thr Ala Tyr Asn Gln Lys Phe
         50                  55                  60

Lys Gly Lys Ala Ile Leu Thr Ala Asp Lys Ser Ser Ser Thr Ala Tyr
 65                  70                  75                  80

Met Glu Leu Arg Ser Leu Thr Ser Glu Asp Ser Ala Val Tyr Tyr Cys
                    85                  90                  95

Thr Arg

<210> SEQ ID NO 26
<211> LENGTH: 113
<212> TYPE: PRT
<213> ORGANISM: Artificial Sequence
<220> FEATURE:
<223> OTHER INFORMATION: Hu IGHV1-18/HJ4 vH
```

<400> SEQUENCE: 26

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Phe Asp Tyr Trp Gly Gln Gly Thr Leu Val Thr Val Ser
                100                 105                 110

Ser
```

<210> SEQ ID NO 27
<211> LENGTH: 113
<212> TYPE: PRT
<213> ORGANISM: Artificial Sequence
<220> FEATURE:
<223> OTHER INFORMATION: Hu IGHV1-69-2/HJ4 vH

<400> SEQUENCE: 27

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
                20                  25                  30

Tyr Met His Trp Val Gln Gln Ala Pro Gly Lys Gly Leu Glu Trp Met
            35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Tyr Phe Asp Tyr Trp Gly Gln Gly Thr Leu Val Thr Val Ser
                100                 105                 110

Ser
```

<210> SEQ ID NO 28
<211> LENGTH: 100
<212> TYPE: PRT
<213> ORGANISM: Artificial Sequence
<220> FEATURE:
<223> OTHER INFORMATION: Mu IGKV1-117

<400> SEQUENCE: 28

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
```

```
                    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro
            100

<210> SEQ ID NO 29
<211> LENGTH: 112
<212> TYPE: PRT
<213> ORGANISM: Artificial Sequence
<220> FEATURE:
<223> OTHER INFORMATION: Hu IGKV2-30/KJ2 vL

<400> SEQUENCE: 29

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Tyr Thr Phe Gly Gln Gly Thr Lys Leu Glu Ile Lys
            100                 105                 110

<210> SEQ ID NO 30
<211> LENGTH: 580
<212> TYPE: PRT
<213> ORGANISM: Artificial Sequence
<220> FEATURE:
<223> OTHER INFORMATION: huGPC3 FL

<400> SEQUENCE: 30

Met Ala Gly Thr Val Arg Thr Ala Cys Leu Val Val Ala Met Leu Leu
 1               5                  10                  15

Ser Leu Asp Phe Pro Gly Gln Ala Gln Pro Pro Pro Pro Pro Pro Asp
                20                  25                  30

Ala Thr Cys His Gln Val Arg Ser Phe Phe Gln Arg Leu Gln Pro Gly
            35                  40                  45

Leu Lys Trp Val Pro Glu Thr Pro Val Pro Gly Ser Asp Leu Gln Val
 50                  55                  60

Cys Leu Pro Lys Gly Pro Thr Cys Cys Ser Arg Lys Met Glu Glu Lys
 65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
            115                 120                 125

Met Phe Lys Asn Asn Tyr Pro Ser Leu Thr Pro Gln Ala Phe Glu Phe
 130                 135                 140
```

-continued

```
Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
            165                 170                 175

Val Ile Tyr Thr Gln Leu Met Asn Pro Gly Leu Pro Asp Ser Ala Leu
        180                 185                 190

Asp Ile Asn Glu Cys Leu Arg Gly Ala Arg Arg Asp Leu Lys Val Phe
    195                 200                 205

Gly Asn Phe Pro Lys Leu Ile Met Thr Gln Val Ser Lys Ser Leu Gln
210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
            245                 250                 255

Thr Arg Met Trp Tyr Cys Ser Tyr Cys Gln Gly Leu Met Met Val Lys
        260                 265                 270

Pro Cys Gly Gly Tyr Cys Asn Val Val Met Gln Gly Cys Met Ala Gly
    275                 280                 285

Val Val Glu Ile Asp Lys Tyr Trp Arg Glu Tyr Ile Leu Ser Leu Glu
290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
            325                 330                 335

Asn Ala Gly Lys Leu Thr Thr Thr Ile Gly Lys Leu Cys Ala His Ser
        340                 345                 350

Gln Gln Arg Gln Tyr Arg Ser Ala Tyr Tyr Pro Glu Asp Leu Phe Ile
    355                 360                 365

Asp Lys Lys Val Leu Lys Val Ala His Val Glu His Glu Glu Thr Leu
370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
            405                 410                 415

Glu Asn Asp Thr Leu Cys Trp Asn Gly Gln Glu Leu Val Glu Arg Tyr
        420                 425                 430

Ser Gln Lys Ala Ala Arg Asn Gly Met Lys Asn Gln Phe Asn Leu His
    435                 440                 445

Glu Leu Lys Met Lys Gly Pro Glu Pro Val Val Ser Gln Ile Ile Asp
450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
            485                 490                 495

Asp Cys Gly Asp Asp Glu Asp Glu Cys Ile Gly Gly Ser Gly Asp Gly
        500                 505                 510

Met Ile Lys Val Lys Asn Gln Leu Arg Phe Leu Ala Glu Leu Ala Tyr
    515                 520                 525

Asp Leu Asp Val Asp Asp Ala Pro Gly Asn Ser Gln Gln Ala Thr Pro
530                 535                 540

Lys Asp Asn Glu Ile Ser Thr Phe His Asn Leu Gly Asn Val His Ser
545                 550                 555                 560
```

-continued

```
Pro Leu Lys Leu Leu Thr Ser Met Ala Ile Ser Val Val Cys Phe Phe
            565                 570                 575
Phe Leu Val His
        580
```